(12) United States Patent
Okamura

(10) Patent No.: US 8,872,127 B2
(45) Date of Patent: Oct. 28, 2014

(54) BEAM CURRENT CONTROLLER FOR LASER ION SOURCE

(75) Inventor: Masahiro Okamura, Sound Beach, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 13/398,553

(22) Filed: Feb. 16, 2012

(65) Prior Publication Data

US 2012/0211668 A1 Aug. 23, 2012

Related U.S. Application Data

(60) Provisional application No. 61/445,322, filed on Feb. 22, 2011.

(51) Int. Cl.
*H01J 27/24* (2006.01)
*H05H 1/10* (2006.01)
*A61N 5/10* (2006.01)
*H05H 7/08* (2006.01)

(52) U.S. Cl.
CPC ......... *H01J 27/24* (2013.01); *A61N 2005/1074* (2013.01); *H05H 2007/082* (2013.01); *A61N 5/10* (2013.01); *A61N 2005/1088* (2013.01)
USPC ..................................... 250/425; 250/423 R

(58) Field of Classification Search
USPC ............... 250/423 R–426; 313/153; 315/505
See application file for complete search history.

(56) References Cited

U.S. PATENT DOCUMENTS

| | | | |
|---|---|---|---|
| 4,987,007 A * | 1/1991 | Wagal et al. | 427/526 |
| 6,744,225 B2 | 6/2004 | Okamura et al. | |
| 7,432,516 B2 * | 10/2008 | Peggs et al. | 250/492.3 |
| 2002/0093653 A1 * | 7/2002 | Detalle et al. | 356/318 |
| 2002/0096427 A1 * | 7/2002 | Lu et al. | 204/192.12 |
| 2002/0166960 A1 * | 11/2002 | Pronko et al. | 250/282 |
| 2004/0011280 A1 * | 1/2004 | Higuchi et al. | 117/97 |
| 2008/0264341 A1 * | 10/2008 | Druz et al. | 118/723 MP |
| 2009/0277585 A1 * | 11/2009 | Maebashi et al. | 156/345.28 |
| 2009/0289194 A1 * | 11/2009 | Saito | 250/396 R |

OTHER PUBLICATIONS

Okamura et al, "Laser Ion Source for Low-Charge Heavy Ion Beams", Nuclear Instruments and Methods in Physics Research A, 606 (2009) 94-96.*
Okumura et al, "Laser Ion SOurce for Low-Charge Heavy Ion Beams", Nuclear Instruments and Methods in Physics Research A, 606 (2009) 94-96.*
Tillack et al, "Magnetic Confinement of an Expanding Laser-Produced Plasma", 2003, http://aries.ucsd.edu/LIB/REPORT/CONF/IFSA03/MagDiv.pdf).*
Alessi, J., et al., "The Brookhaven National Laboratory Electron Beam Ion Source for RHIC," *Review of Scientific Instruments*, vol. 81, pp. 02A509-1 to 02A509-5, 2010.

(Continued)

*Primary Examiner* — Jack Berman
*Assistant Examiner* — David E Smith
(74) *Attorney, Agent, or Firm* — Dorene M. Price

(57) ABSTRACT

The present invention relates to the design and use of an ion source with a rapid beam current controller for experimental and medicinal purposes. More particularly, the present invention relates to the design and use of a laser ion source with a magnetic field applied to confine a plasma flux caused by laser ablation.

38 Claims, 23 Drawing Sheets

(56) References Cited

OTHER PUBLICATIONS

Kanesue, T., et al., "Feasibility Study of a Laser Ion for Primary Ion Injection into the Relativistic Heavy Ion Collider Electron Beam Ion Source," *Review of Scientific Instruments*, vol. 79, pp. 02B102-1 to 02B102-3, 2008.

Kanesue, T., et al., "Confinement of Laser Plasma by Solenoidal Field Ion Source," 1$^{st}$ International Particle Accelerator Conference (Kyoto, Japan May 23-28, 2010) [online] [retrieved from: <URL: http://epaper.kek.jp/IPAC10/html/author.htm>] Last Accessed Jul. 26, 2013, (3 pages).

Kondo, K., et al., "Design Study of a Primary Ion Provider for Relativistic Heavy Ion Collider Eelctron Beam Ion Source," *Review of Scientific Instruments*, vol. 81, pp. 02A511-1 to 02A511-3, 2010.

Kondo, K., et al., "LIS in Low Power Density for RHIC-EBIS," 1$^{st}$ International Particle Accelerator Conference (Kyoto, Japan May 23-28, 2010) [online] [retrieved from: <URL: http://epaper.kek.jp/IPAC10/html/author.htm>] Last Accessed Jul. 26, 2013, (3 pages).

Kondo, K., et al., "Angular Distribution of Laser Ablation Plasma," [retrieved from: <URL: http://epaper.kek.jp/IPAC10/html/author.htm>] Last Accessed Jul. 26, 2013, (3 pages).

Okamura, M., et al., "Laser Ion Source for Low-Charge Heavy Ion Beams," *Nuclear Instruments and Methods in Physics Research A*, vol. 606, pp. 94-96, 2009.

Okamura, M., et al., "Magnetic Plasma Confinement for Laser Ion Source," *Review of Scientific Instruments*, vol. 81, pp. 02A510-1 to 02A510-3, 2010.

Petti, P., et al., "Hadronic Radiotherapy," *Annual Review of Nuclear and Particle Science*, vol. 44, pp. 155-197, 1994 [online] [retrieved Jul. 26, 2013 from: <URL: http://www.annualreviews.org>].

Sharkov, B., "*Laser Ion Sources*," Chapter 12 of "The Physics and technology of Ion Sources," (Wiley-VCH, 2004) pp. 233-255, with title and bibliographic page.

Wangler, T., "*Radiofrequency Quadruple Linae*," Chapter 8 of "RF Linear Accelerators." (Wiley-VCH, 2008, Germany) pp. 232-281, with title and bibliographic page.

\* cited by examiner

BEAM CURRENT CONTROLLER FOR LASER ION SOURCE

CROSS-REFERENCE TO A RELATED APPLICATION

This application claims the benefit under 35 U.S.C. 119(e) of U.S. Provisional Application No. 61/445,322 filed on Feb. 22, 2011, the content of which is incorporated herein in its entirety.

STATEMENT OF GOVERNMENT LICENSE RIGHTS

This invention was made with Government support under contract number DE-AC02-98CH10886, awarded by the U.S. Department of Energy. The Government has certain rights in the invention.

BACKGROUND OF THE INVENTION

I. Field of the Invention

The design and manufacture of an ion source is provided with a rapid beam current controller for experimental and medicinal purposes. More particularly, the design and manufacture of a laser ion source is provided with a magnetic field applied to confine a plasma flux caused by a laser ablation.

II. Background of the Related Art

High-energy ionizing radiation has continuously been used in high energy physics for the last half a century. More recently, however, high-energy ionizing radiation has shown promising results in the medical field and, in particular, in the treatment of cancerous tumors because hadronic matter, i.e., protons and light ions (e.g., carbon), have the advantage of easily penetrating the body and then depositing their energy at a depth immediately before the particles/ions come to rest determined by "Bragg peak." The light ions also have shown an increased relative biological effectiveness in treating cancerous tumors. Due to these advantages as compared to conventional radiotherapy, hadron therapy facilities have been build with increased frequency.

The use of different hadron beams needs the availability of powerful ion sources which are time-stable and provide high-quality beams of different light ions. At present, electron cyclotron resonance (ECR) ion sources mostly provide the particle beams for hadron therapy. The use of ECR ion sources is based on resonantly coupling microwave power to a plasma by matching the microwave frequency to the electron cyclotron frequency in the magnetic field where the plasma is confined.

Laser ion sources (LIS) have been proposed as an alternative ion source because the LIS has two major advantages over other types of ion sources. The first feature is a high plasma density. The LIS creates plasma from dense solid material, while other types of ion sources normally start from gas. A single laser shot from a conventional tabletop laser can generate a large number of ions. For example, a 2 J Nd—YAG laser shot generates about $2 \times 10^{14}$ ions from an aluminum target. The second advantage is that the laser-produced plasma has an initial expanding velocity normal to the target. The laser-generated ions can be transported in a neutralized plasma state.

To utilize these two advantages, Okamura et al. (*17th Inter. Symp. on Heavy Ion Inertial Fusion*, 2008; incorporated herein by reference in its entirety) proposed a method of combining a laser ion production and injection for use in a low charge state heavy ion production configured as a direct plasma injection scheme or (DPIS). FIG. 1A shows a DPIS scheme of Okamura et al. In this scheme, a solid target 11 is placed in an electrically isolated enclosure 17 biased to HV power supply which is in a vacuum chamber 10. The vacuum chamber 10 is directly connected to a radio frequency quadrupole (RFQ) linear accelerator 30 via a plasma drift section 20. A high power laser 40, i.e., generally between $10^8$ to $10^{13}$ W/cm$^2$, is focused onto the solid-state target 11 through windows 13 via an optical assembly 12 (including a plurality of flat surface mirrors and a convex lens) to produce a dense plasma, which contains highly charged ions. A laser produced plasma adiabatically expands in the direction 15, which is perpendicular to a target surface, as shown in FIG. 1B. Simultaneously, the plasma expands three dimensionally with a large momentum spread. This expansion makes a plasma pulse width longer and a current density smaller. The induced plasma is then pushed out from the enclosure 10 and the plasma drift section 20 into the RFQ cavity 30 through the extraction point 31. Inside the RFQ cavity 30, the ions from the neutral laser plasma are extracted by the electric field and are immediately captured by the RF quadrupole focusing force of the RFQ electrodes 33 within the RFQ. As a result, the high density ion beam is efficiently accelerated through the RFQ.

While laser ion sources are very powerful and can provide low charge state, low emittance and high ion yield, they still suffer from numerous drawbacks especially if a high charge state is desired. For example, although the peak current is high, the pulse width of the beam is too short for some applications such as the acceleration of ions in the synchrotron and it is difficult to change the beam current within a short time frame, a prerequisite for successful hadron therapy. Also, while, the plasma pulse width at the entrance of the RFQ can be extended to increase ion beam pulse width, primarily regulated by extending plasma drift distance, unfortunately, the injected current to the RFQ becomes too small and unworkable.

Therefore, it would be desirable to have a laser ion source (LIS) that overcomes the shortcomings of the prior art including the difficulty of (1) changing the ion beam current on pulse to pulse basis, (2) controlling the ion pulse duration and shape, and (3) independently changing the ion pulse length and the beam current.

SUMMARY OF THE INVENTION

Having recognized the shortcomings of the prior art, as one embodiment, a laser ion source is provided with a magnetic field applied at a plasma drift section to confine plasma flux caused by a laser ablation. In a further embodiment, by introducing rapid control of the magnetic field at the plasma drift section, the diverging angle of the laser plasma can be controlled, and as a result, the beam current and its pulse shape can be manipulated, as demanded, within a very short time duration, for example, on the order of milliseconds. In yet a further embodiment, by manipulating the beam current, the user can manipulate the number of ions on a pulse by pulse basis, a feature for the hadron cancer therapy.

The present laser ion source generally comprises a plasma generating source, a plasma drift section, a linear accelerator, and a rapid beam current controller positioned in the plasma drift section between the plasma generating source and the linear accelerator. Typically, the laser ion source can be configured to be used as a low and/or high charge state ion provider in a synchrotron system, such as rapid-cycling synchrotron. The plasma generating source comprises a target, e.g., graphite, aluminum, silver, etc., confined within an electrically isolated enclosure that upon exposure to a laser light generates a plasma. The rapid beam current controller is a device that generates a magnetic field. Preferably, the rapid beam current controller is a solenoid coil type magnet, although other magnets are also envisioned that would provide a confinement of a plasma flux caused by the laser ablation in the plasma drift section. The ion linear accelerator, e.g., RFQ linac, is a device where the ions are extracted from a plasma by the electric field and captured by a radio frequency quadrupole focusing force.

In another embodiment, a method of controlling a number of ions in a rapid cycling synchrotron is provided. The method comprises generating a plasma on the surface of a target by plasma ablation confined within an electrically isolated enclosure; allowing the generated plasma to pass through a plasma drift section and a rapid beam current controller into a cavity of an ion linear accelerator; adjusting the number of particles reaching the linear accelerator by changing the magnetic field strength of the rapid beam current controller; extracting a plurality of ions from the generated plasma by an electric field in the ion linear accelerator; capturing the generated ions by a radio frequency quadrupole focusing force, and accelerating the generated ions in the ion linear accelerator.

In yet another embodiment, a method of treating cancer using a hadron therapy is provided where initially a plasma is generated on the surface of a target by plasma ablation confined within an electrically isolated enclosure. The generated plasma is then allowed to pass through a plasma drift section into a cavity of an ion linear accelerator. The plasma drift section also includes a rapid beam current controller. The number of particles reaching the linear accelerator are adjusted by changing the magnetic field strength of the rapid beam current controller. Once the particles reach the cavity of the ion linear accelerator, the ions are extracted from the generated plasma by an electric field in the ion linear accelerator. The generated ions can then be captured by a radio frequency quadrupole focusing force and accelerated in the ion linear accelerator. The accelerated ions are subsequently injected and further accelerated in a synchrotron. Once the ions reach a desired beam energy in the synchrotron, they are diverted and passed through a medical gantry towards a patient in need of treatment. When these ions come in contact with the cancerous tissue in the patient, it is envisioned that the cancerous tissue/cells will be killed or damaged.

The present objectives, features and advantages will be apparent from the following detailed description of the invention, which is to be read in conjunction with the accompanying drawings. The scope of the invention will be pointed out in the claims. The following drawings, taken in conjunction with the subsequent description, are presented to enable one of ordinary skill in the art to make and use the invention and to incorporate it in the context of particular applications.

DETAILED DESCRIPTION OF THE INVENTION

A laser ion source (LIS) is provided with a magnetic field applied at a plasma drift section to confine plasma flux caused by a laser ablation. The present laser ion source generally comprises a rapid beam current controller, which by virtue of a magnetic field confines a plasma flux. In a further embodiment, by introducing rapid control of the magnetic field at the plasma drift section, the diverging angle(s) of the laser generated plasma can be controlled, and as a result, the beam current and its pulse shape can be manipulated, as demanded, within a very short time frame, for example, on the order of milliseconds. In yet a further embodiment, by manipulating the beam current, a user can manipulate the number of generated ions on a pulse by pulse basis, a critical feature for the hadron cancer therapy.

Figure 2A:
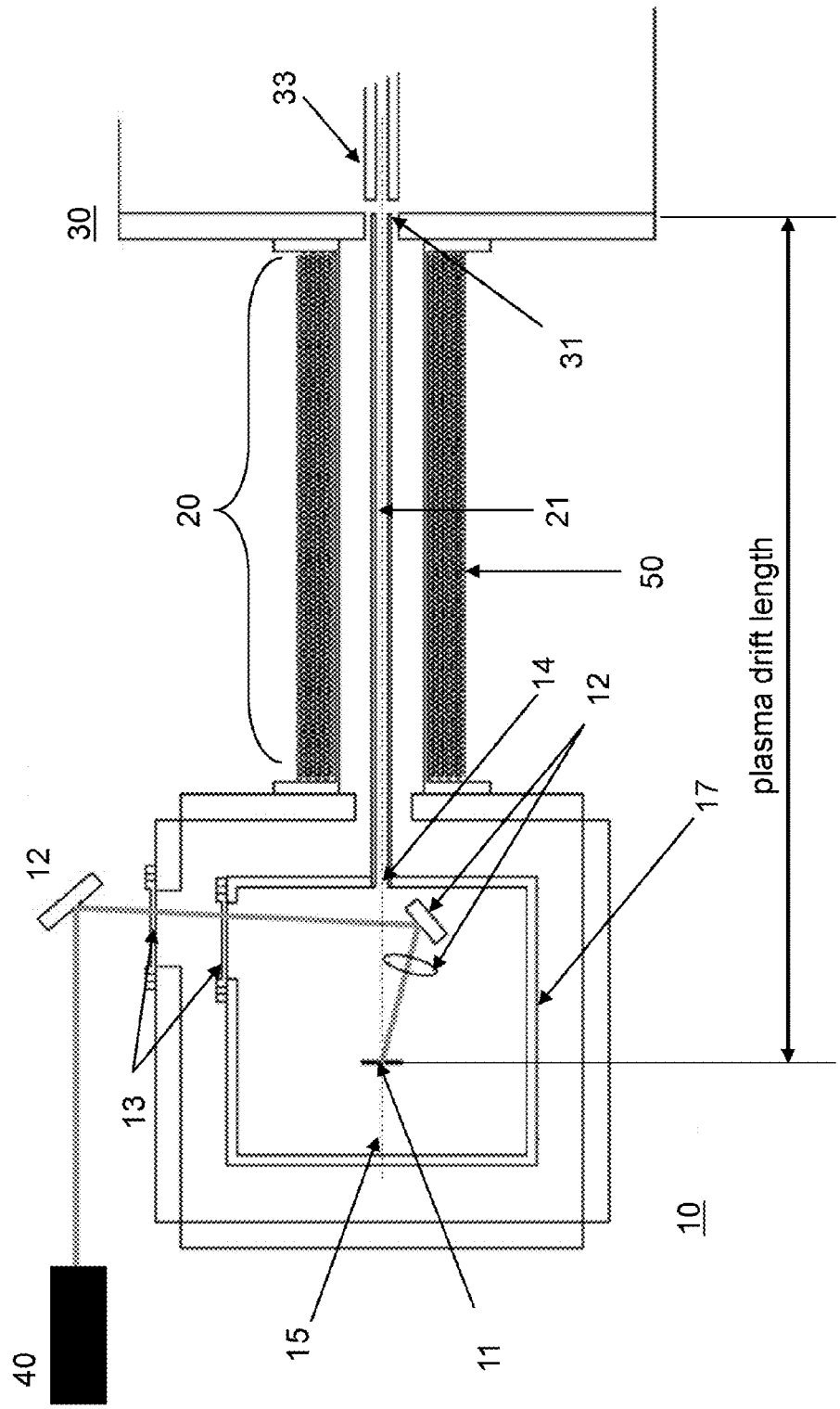
FIG. 2A illustrates an exemplary direct plasma injection scheme (DPIS).

The present laser ion source, as shown in FIG. 2A, comprises a number of individual components or subsystems: (1) a repetitively-pulsed laser 40; (2) an electrically isolated enclosure 10; (3) a target 11 confined within the enclosure 10; (4) an optical focusing assembly 12, (5) a rapid current controller 50; and (6) an ion linear accelerator 30. In one embodiment, the laser ion source is configured as a provider of low and/or high charge state ions for a synchrotron, such as rapid-cycling synchrotron. Each component or subsystem will be considered and described in detail herein below.

A Repetitively-Pulsed Laser Source

The laser-plasma scaling laws for charge state distribution, plasma density, and plasma velocity impose requirements on the minimum laser energy necessary to produce the required ion charge state and other beam parameters in the LIS system. A detailed explanation of how to select a laser for the LIS depending on the target selected and the minimum laser energy necessary to produce the required ion charge state is disclosed in *The Physics and Technology of Ion Sources* by Ian Brown (Chapter 12, Wiley-VCH; 2nd ed., 2004; incorporated herein by reference in its entirety). In one embodiment, a laser used for the present LIS (see FIG. 2A; laser 40) has about 0.1 to 100 J output energy and can typically generate laser pulses with duration from about 5 ns to about 100 ns at the repetition rate of up to about 50 Hz. The laser typically generates a laser beam that ranges between 1 mm and 300 mm in diameter, with 8 mm to 14 mm diameter being preferred. In one embodiment, the laser source is $CO_2$ laser, Nd:YAG laser, or Ti:Sapphire laser.

An Electrically Isolated Enclosure

Once the laser light has been generated by the laser 40, it typically enters the electrically isolated enclosure 10 through one or more windows 13 that are transparent to the laser wavelength of interest. For example, if the laser selected is an Nd type laser or Ti Safire laser, its wavelength is about 1.06 μm, which means a glass window, such as a coated glass or BK7, can be used. However, if the selected laser is a $CO_2$ laser, its wavelength is about ten times longer or about 10.64 μm. For such a laser, a glass window will not work due to its high absorbance in the IR range. Therefore, a salt window, e.g., NaCl or ZnSe, can be used. Although, it is also conceivable that the laser source can be placed within the enclosure and, therefore, the window would not be necessary.

The electrically isolated enclosure 17 is made from a conductive metallic or nonmetallic material such as stainless steel of about 0.5 mm to 1.0 mm thickness, and insulated from ground to a potential of up to about 100 kV. The electrically isolated enclosure is surrounded by a vacuum chamber that can be pumped down to $10^{-6}$ Torr, with a range of $10^{-6}$ Torr to $10^{-8}$ Torr being preferred, after each laser shot with a repetition rate of 1-100 Hz. The enclosure has dimensions sufficient to ensure the proper placement of the target 11 and any other desired components, e.g., optical focusing assembly 12 or a portion thereof. In one embodiment, the enclosure can have a hexahedron shape with each side having a length of 300 to 700 mm. In an exemplary embodiment shown in FIG. 2A, the enclosure 10 has a hexahedron shape with each side having the length of about 400 mm. However, it is also envisioned that the shape of the enclosure is not necessarily a hexahedron shown in FIG. 2A and may also encompass round shapes e.g., see FIG. 15, or any other shapes. The enclosure 10 can further comprise an unobstructed opening 14 connected with a plasma drift section 20 to allow the generated plasma to drift from the enclosure 10 into the plasma drift section 20 of the LIS.

Optical Focusing Assembly

In one embodiment, the LIS further comprise an optical focusing assembly 12 of mirrors and lenses, positioned between the laser source 40 and the target 11 to guide the laser light from the laser to the target. For example in exemplary embodiment shown in FIG. 2A, the laser light generated by the laser 40 does not directly hit the target but initially may be diverted through a plurality of mirrors and a plurality of lenses. In FIG. 2A, the laser light (solid line) initially encounters a mirror placed at about 45 degrees to the direction of the laser light in order to change the direction of the light and allow it to enter the enclosure 10 through the window 13. Once inside the enclosure 10, in this embodiment, the light encounters another mirror that is positioned to divert the light towards the target 11 with the incidental angle of about 10-40 degrees, with about 30 degrees being preferred. The laser light then passes through a convex lens to focus the light on the target 11. Preferably, the convex lens would focus the laser light on the target to create a laser beam having a diameter from 0.1 to 0.2 mm and energy output from $10^{11}$ to $10^{12}$ $J/cm^2$.

All or a portion of the mirrors and lenses can be placed outside the enclosure or can be confined within the enclosure to insure a proper alignment of the laser light. For example, in configurations shown in FIG. 12A and FIG. 15, the optical focusing assembly is placed outside the enclosure, whereas in a configuration shown in FIG. 2A, a portion of the optical focusing assembly is placed inside the enclosure.

A Target Confined within the Enclosure

The electrically isolated enclosure 17 further comprises a target 11 that upon exposure to a laser light generates a plasma. Typically, the target 11 is placed at the longitudinal axis 15 of the opening 14 in the enclosure 10, the plasma drift section cavity 21 and the electrodes 33 of the linear accelerator 30. As illustrated in FIG. 2A, the longitudinal axis 15 is provided as a dashed line from the target 11 towards the linear accelerator 30.

Any ionizable solid material can be used for the target as the source of ions and primarily is selected depending on the ions desired. For example, for the hadron therapy, the desired ions are carbon or proton particles. Thus, the target can be, but not limited to, a graphite (C) as carbon ion source or Ti—H as proton ion source. For other purposes, the target can be, but is not limited to, Al, Si, Fe, Ta, Ag, Au, Ge, Pb, Cu, Ti, Pt, U, frozen Ne, or frozen Ar. The dimensions of the target are determined by the number of laser pulses required before the target replacement would be necessary. For example, for a high charge ion production, a typical crater size, i.e., a position of a laser contact, is about 0.2 mm in diameter. If the target has a square shape, 250 mm×250 mm, the target can accommodate more than $1.5 \times 10^6$ shots before replacement. For low charge state production, the target can accommodate significantly more shots, for example, more than one thousand laser shots in each position/crater. The basic principle of laser plasma generation and a detailed analysis of the Inverse Bremsstrahlung mechanism (an absorption process due to the scattering of plasma electrons accelerated in the light) are described in *The Physics and Technology of Ion Sources* by Ian Brown (Chapter 12, Wiley-VCH; 2nd ed., 2004), which is incorporated herein by reference in its entirety.

A Rapid Current Controller

The rapid beam current controller 50 is positioned in the plasma drift section 20 between the electrically isolated enclosure 10 and the ion beam extraction point 31 defined by the entrance of the ion accelerator 30. The rapid beam current controller 50 is a device that generates a magnetic field, preferably by an action of a solenoid coil type magnet. However, other magnets are also envisioned that may be suitable for the LIS of the present invention as long as a plasma flux caused by the laser ablation in the plasma drift section can be confined by its generated magnetic field.

Figure 4:
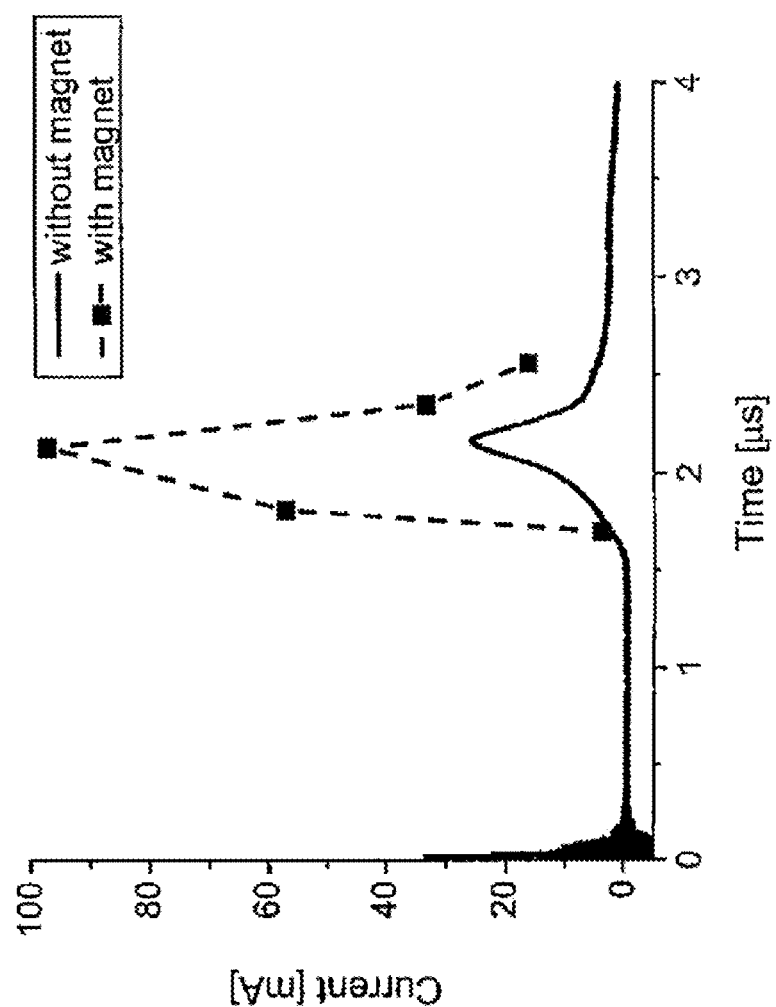
FIG. 4 compares a measured current density without a magnet and a predicted current density with a magnet.

In a preferred embodiment, the magnetic field is generated by a solenoid. The solenoid is a metal wire wound into a tightly packed helix. In one embodiment, the metal wire has diameter from about 0.1 mm to about 10 mm. The tightly packed helix can have a diameter from 10 mm to 500 mm, with 100 mm being preferred. The length of the solenoid can range from 10 mm to 10 m, whereas the total drift length can range from 200 mm to 10 m. In a preferred embodiment, the ratio of the plasma drift length to the solenoid length is between about 1:1 and 10:1 and anything therebetween. In a more preferred embodiment, the ratio of the plasma drift length to the solenoid length is about 3:1 or higher. FIG. 4 shows exemplary parameters of a solenoid magnet.

The distance between the target and the ion beam extraction point is defined by the plasma drift length. The pulse duration of the ion beam extracted from a laser ion source is determined by the plasma drift length because of the energy spread of the plasma during its expansion. In most laser ion sources, the relationship between current density, plasma drift length, beam pulse duration, and particle number can be described by Eqns. (1)-(3), $$j \propto L^{-3}, \quad (1)$$

$$t \propto L, \quad (2)$$

$$N \propto L^{-2}, \quad (3)$$

where j, L, t, and N are current density, plasma drift length, beam pulse duration, and particle number, respectively. Longer drift distance reduces not only current density but also particle number. With the enhancement factor ($\alpha$) due to an application of a magnetic field in the plasma drift section, the relationships can be rewritten as, $$j \propto \alpha L^{-3}, \quad (4)$$

$$N \propto \alpha L^{-2}, \quad (5)$$

Figure 1A:
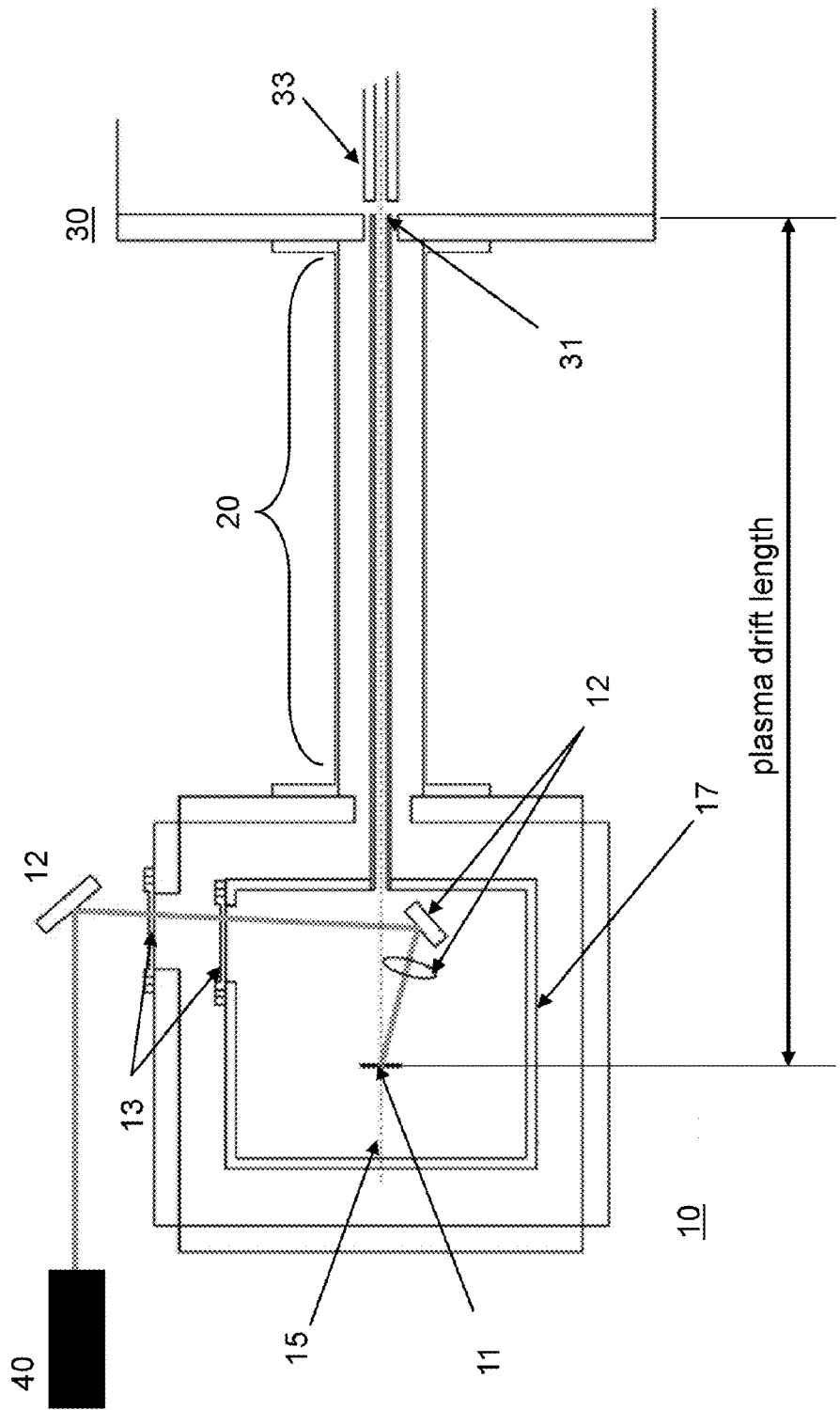
FIG. 1A illustrates a Prior Art direct plasma injection scheme (DPIS) disclosed in Okamura et al. (2008).
Figure 1B:
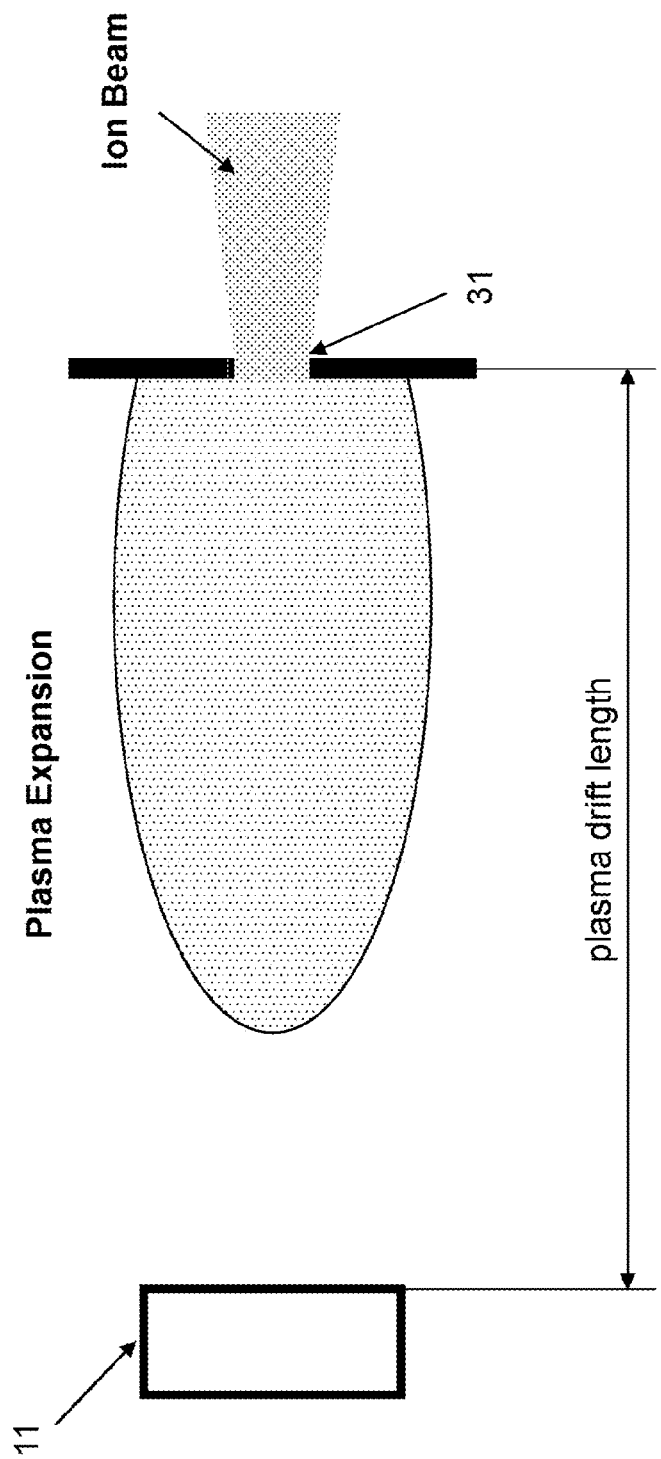
FIG. 1B illustrates an expanding plasma from the target towards the ion extraction point in the Prior Art DPIS of Okamura et al. (2008).
Figure 2B:
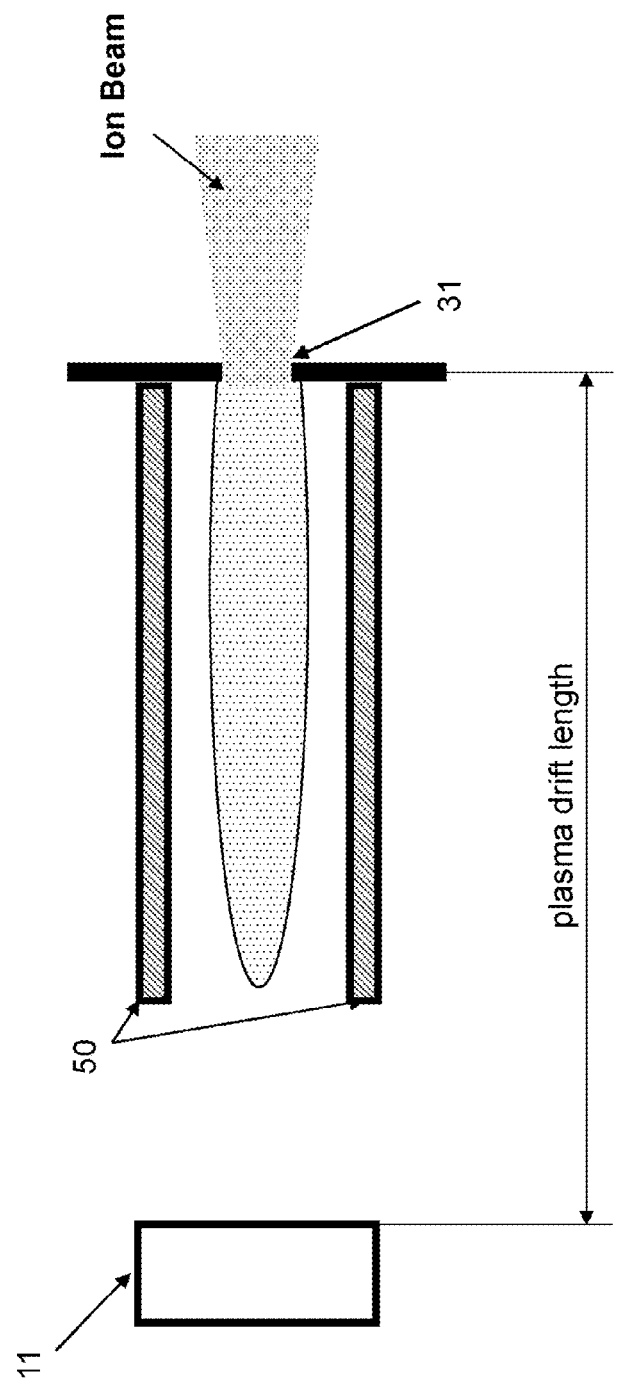
FIG. 2B illustrates an expending plasma from the target towards the ion extraction point in the DPIS.

However, the relationship of pulse length t does not depend on the magnetic field and therefore Eqn. (2) remains the same. As shown in FIG. 2B, the application of the magnetic field flux in the plasma drift section confines the electrons, thus creating an electrically negative potential volume. The magnetic field flux in the plasma drift section can also produce a strong current enhancement effect at the plasma expansion space because the ions emitted from the targets are not only influenced by the magnetic field but also guided by the electrical potential induced by the electron stream. The electrons have almost the same velocities as the ions. Therefore, the electrons have to follow the direction of the magnetic field flux and boost the focusing effect of the rapid current controller. As a result, the diverging angle of the plasma (see FIG. 1B and FIG. 2B) can be manipulated based on the amount of the current passing through the solenoid and the magnetic field produced by the solenoid. Use of the solenoid, therefore, can control the beam current and its pulse shape, as demanded, within a very short time frame, for example, on the order of milliseconds. In turn, by manipulating the beam current, the number of ions can be changed on a pulse by pulse basis, which is a critical feature for the hadron cancer therapy.

An Ion Linear Accelerator

The linear ion accelerator (or linac) component of the LIS extracts ions from the plasma and immediately accelerates them. In a preferred embodiment, the linear accelerator is a radio frequency quadrupole (RFQ) accelerator that has a strong transverse focusing force. Once a beam is captured by the transverse force, the modulation pattern on the RFQ electrodes (see FIG. 2A, electrodes 33 positioned within the RFQ 30) produces an accelerating force in the axial direction and the beam is combined gradually to form an acceleration bucket. A detailed discussion of various linac designs including RFQ designs are provided in *RF Linear Accelerators* by Thomas Wangler (Chapter 8, Wiley-VCH Verlag GmbH, Weinheim 2008; incorporated herein by reference in its entirety).

A Method of Controlling a Number of Ion Particles

One of the requirements for the ion source used in the rapid cycling synchrotron is the ability of the ion source to rapidly change the number of ion particles produced and accelerated by the synchrotron. By varying the plasma drift length, the plasma parameters in the ion source can be changed to control the induced particle number. However, the injected beam properties are also affected and cause an additional need to tune the subsequent accelerator components in the particle acceleration chain.

In one embodiment, a method of controlling a number of ion particles in the rapid cycling synchrotron is provided. The method comprises generating a plasma on the surface of a target by plasma ablation confined within an electrically isolated enclosure; allowing the generated plasma to pass through a plasma drift section with a rapid beam current controller into a cavity of an ion linear accelerator; adjusting the number of particles reaching the linear accelerator by changing the magnetic field strength of the rapid beam current controller; extracting a plurality of ions from the generated plasma by an electric field in the ion linear accelerator; capturing the generated ions by a radio frequency quadrupole focusing force, and accelerating the generated ions in the ion linear accelerator.

The magnetic field generated by the rapid beam controller, e.g., solenoid, placed between the target and the extraction point overcomes the difficulties associated with producing the induced particle number based on varying the plasma parameters of the ion source. The magnetic field strength can be changed within milliseconds, for example, by varying the current passing through the solenoid. The magnetic field, in turn, manipulates the number of ions supplied by a single laser pulse/shot. Since, the magnetic field is applied after plasma production area, only the ion density is changed. Whereas, most of the beam parameters including pulse length, charge state distribution, plasma temperature and emittance are conserved, thus making the present laser ion source readily applicable for use with the rapid cycling synchrotron.

In yet another embodiment, a method of treating cancer using a hadron therapy is provided. The method comprises generating a plasma on the surface of a target by plasma ablation confined within an electrically isolated enclosure; allowing the generated plasma to pass through a plasma drift section with a rapid beam current controller into a cavity of an ion linear accelerator; adjusting the number of particles reaching the linear accelerator by changing the magnetic field strength of the rapid beam current controller; extracting a plurality of ions from the generated plasma by an electric field in the ion linear accelerator; capturing the generated ions by a radio frequency quadrupole focusing force and accelerating them in the ion linear accelerator; injecting the accelerated ions into a synchrotron, such as a rapid cycling synchrotron, accelerating the ions by the synchrotron to a desired beam energy, as it becomes necessary, diverting and passing the ions through a medical gentry towards a patient in need of treatment; and irradiating a cancerous tissue in the patient, thereby, killing or damaging cancerous cells. A general overview of the hadronic radiotherapy is provided in Petty and Lenox *Ann. Rev. Nuclear & Particle Science,* 1994, 44:154-197, which is incorporated herein by reference in its entirety.

EXAMPLES

The examples set forth below serve to provide further appreciation of the invention but are not meant in any way to restrict the scope of the invention.

Example 1

Figure 3:
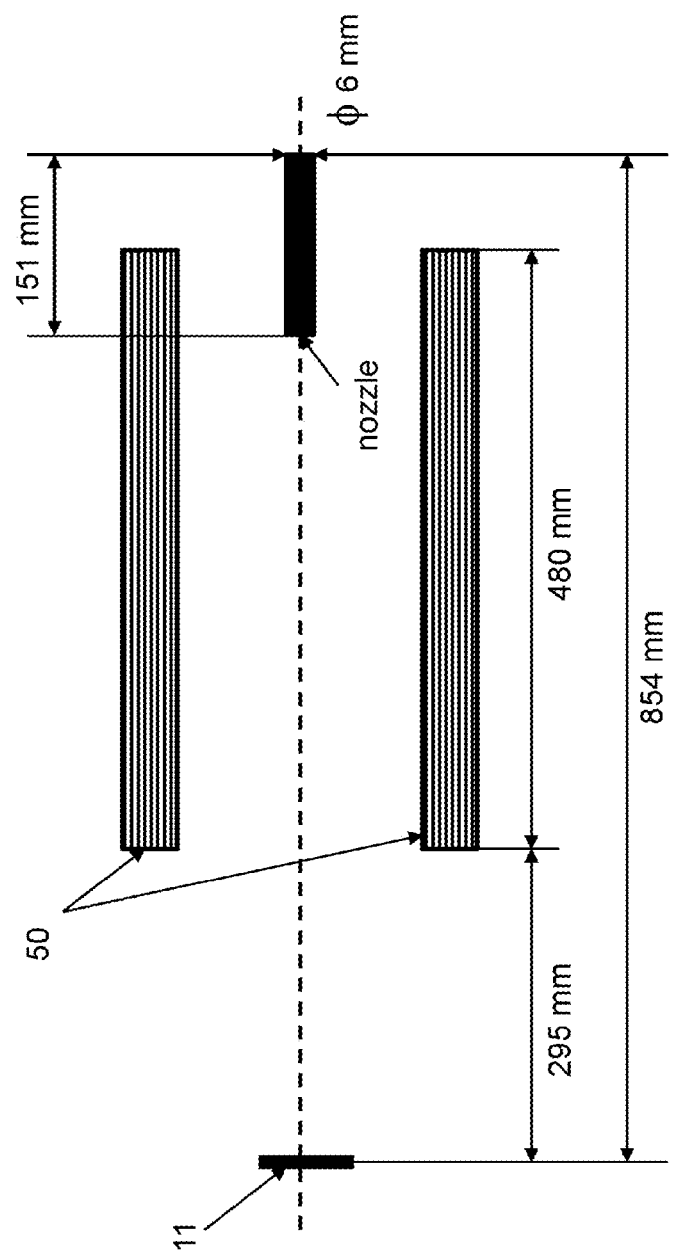
FIG. 3 illustrates an exemplary geometry of the laser ion source scheme with a solenoid used in the OPERA simulations.

Computer simulations were undertaken using OPERA postprocessor software (Vector Fields, Cobham, www.vectorfields.com) to test whether the beam pulse can be manipulated by the magnetic field provided in the plasma drift section of the LIS. To design a solenoid, a simple DPIS geometry shown in FIG. 3 was considered with a carbon beam (charge state 6+) simulated from the target. The length of the simulated solenoid was set to 480 mm and the total drift length was set to 854 mm, which was given by a combination of existing vacuum pipes. In DPIS, a thin pipe guides the expanding plasma to the beam extraction area formed by the RFQ electrodes and the end of the pipe. The inner diameter and the length of the pipe were set to 6 mm and 151 mm, respectively as shown in FIG. 3.

Figure 5:
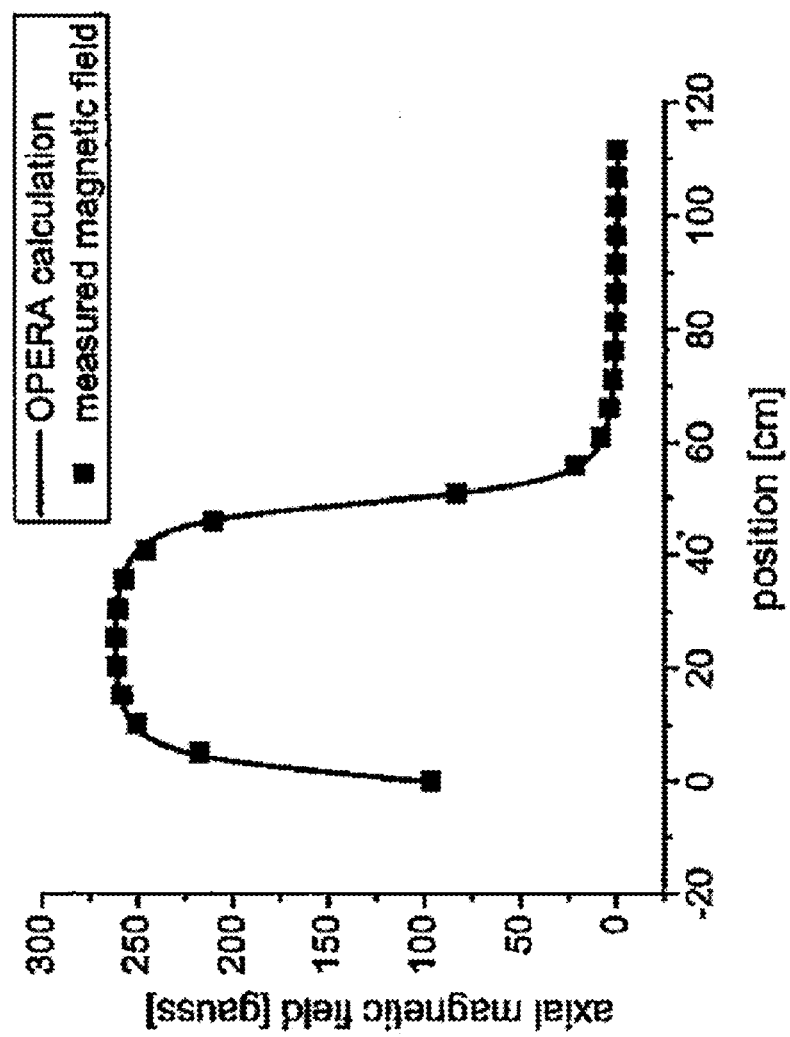
FIG. 5 illustrates a correlation between the measured magnetic field of the solenoid and the predicted magnetic field.

In accordance with this configuration, the Larmor precession radius of the ion orbit had to be reasonably small compared with the pipe size, and only the plasma accommodated by the pipe could reach the extraction point. The assumed current density of the coil was set to 500 A/cm$^2$, that corresponds to 1000 G at the center of the magnet (see FIG. 4). The laser used in the simulation was a Nd—YAG (yttrium aluminum garnet) laser with a power of 1.83 J per shot and the incident angle of the laser beam was set to 30° from normal to the target. The major content of the peak was C$^{6+}$. The current height was converted assuming the diameter was within 6 mm at 854 mm from a graphite target. The predicted enhanced current by the solenoid is shown as dots in FIG. 4. The coil was wound using 2 mm diameter wire directly on a beam pipe. The fabricated coil's inner diameter was set to 76 mm. The OPERA calculation compares well with the measured field of the solenoid as shown in FIG. 5.

Example 2

Figure 6:
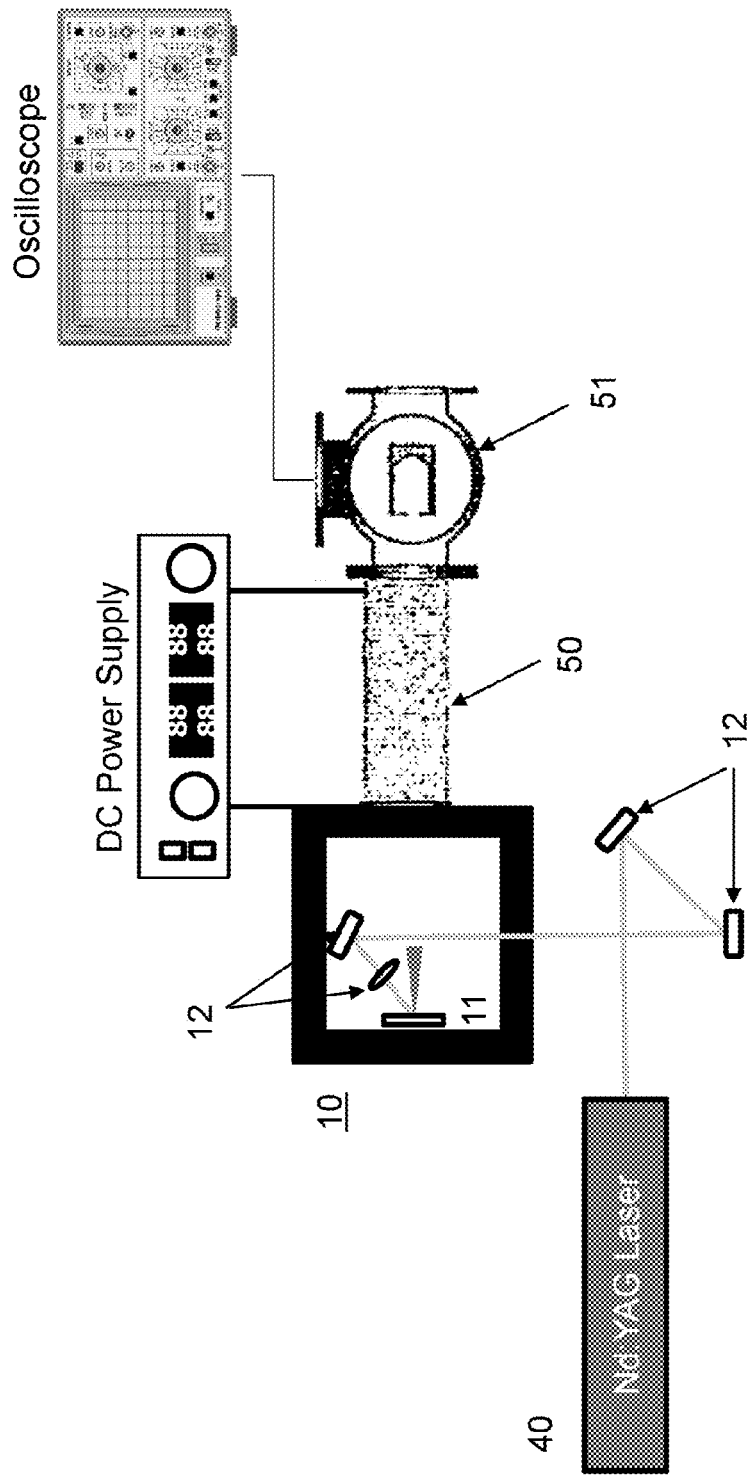
FIG. 6 illustrates an exemplary configuration used to observe the effect of the solenoid, a graphite target and other components.

To observe the effect of the solenoid 50, the DPIS components of Example 1 were assembled as shown in FIG. 6. A suppressor mesh was placed before the Faraday cup 51 to distinguish the ions from the laser plasma. To avoid a breakdown between the suppression mesh and the Faraday cup, a collimator was installed 803 mm away from the target and had an opening diameter of 1.55 mm. The laser power was set to 0.9 J and the laser pulse duration was set to 7 ns (full width at half maximum). The thin plasma guide pipe, as shown in FIG. 3 and discussed in Example 1 was not installed to simplify the experiment.

Figure 7:
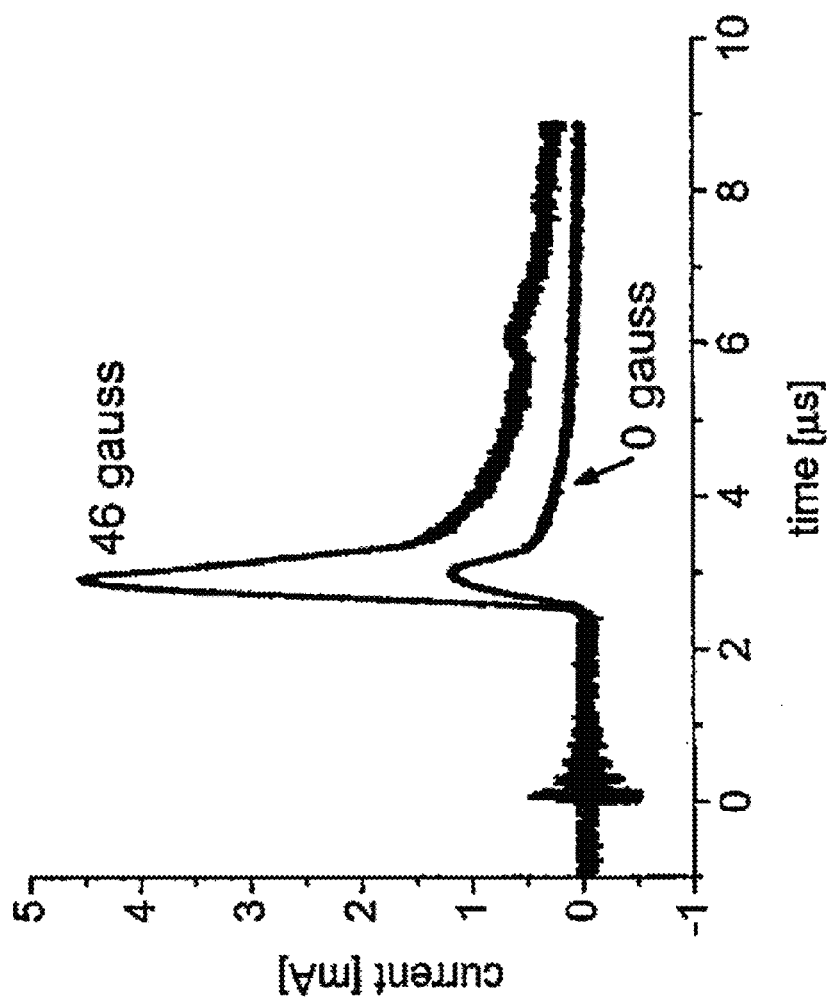
FIG. 7 illustrates an enhanced current waveform of the multicharged carbon beam.
Figure 8:
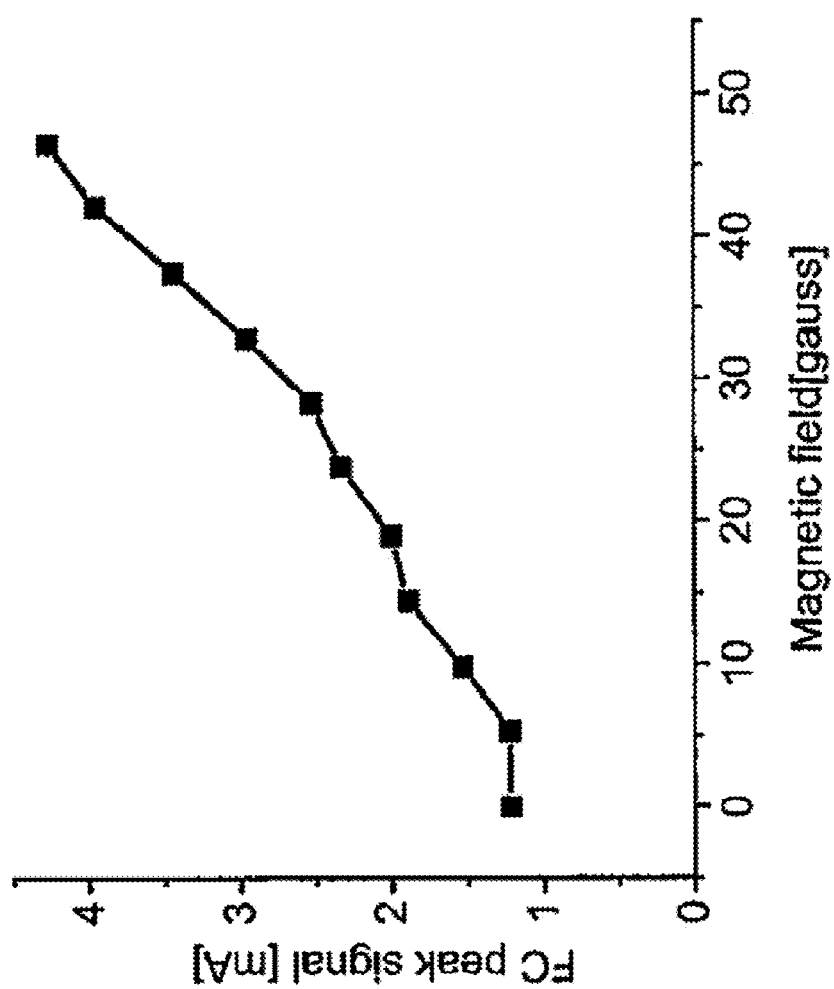
FIG. 8 illustrates a relationship between a peak current and a magnetic field strength of the solenoid.

A typical current waveform taken by the Faraday cup and recorded by an oscilloscope is shown in FIG. 7. The charge states distributed from 3+ to 6+ with the highest yield of charge state 4+. The peak currents obtained from measurements were then plotted in FIG. 8. As shown in FIG. 8, above 50 G, the plasma current density became too high to go through the biased mesh having a voltage of −4.5 keV. The behavior of the plasma current density indicates that the ions and the electrons are not separated and the space charge repulsion force can still be compensated under the presence of the axial magnetic field.

Example 3

Figure 9:
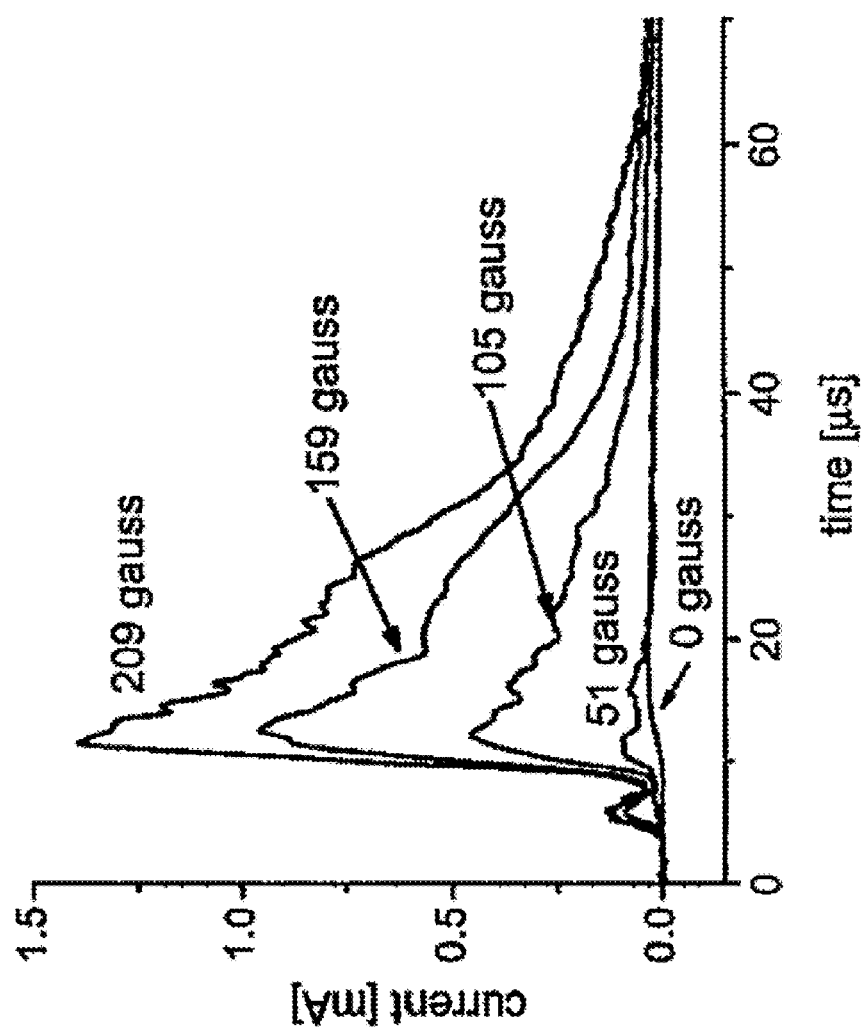
FIG. 9 illustrates $C^{1+}$ beam through the solenoid field.
Figure 10:
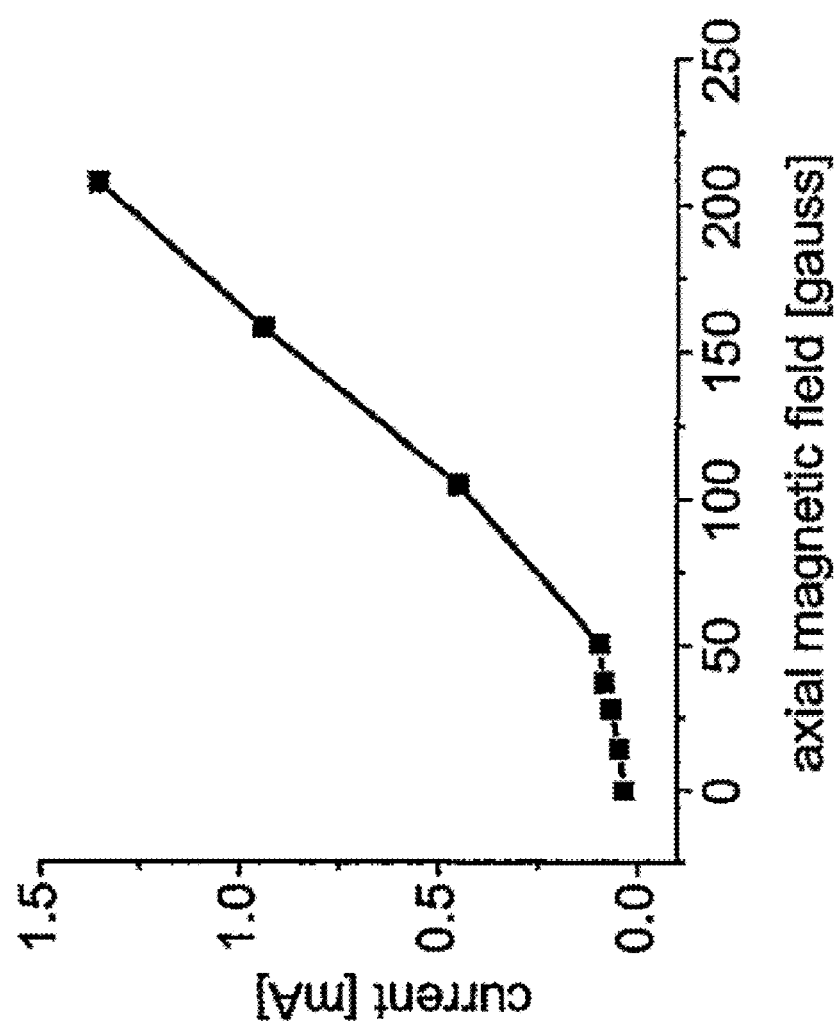
FIG. 10 illustrates a peak current of $C^{1+}$ peak as a function of the magnetic field strength.

A singly charged ion beam was tested using the same design as described in Example 2, except that the opening diameter of the collimator was changed to 2.9 mm from 1.5 mm. The laser power density was adjusted to 2.5×10$^8$ W/cm$^2$ to provide a beam charge state of 1+. The spot diameter on the target was set to 7.6 mm. The measured variation of the current waveform and the peak currents are shown in FIG. 9 and FIG. 10, respectively. In particular, FIG. 10 shows no significant current enhancement up to 50 G. However, above 100 G, the current increased significantly from about 0.5 mA to about 1.5 mA. In particular, at 209 G, the current was amplified about forty times, which was much larger than the predicted current enhancement based on the simple ion trajectory simulation shown in Example 1. While, the beam pulse shape was not distorted at any field strength, above 250 G, a discharge was again observed between the biased mesh and the Faraday cup. This result implies that the ions emitted from the targets are not only influenced by the solenoid magnetic field but also guided by the electric potential induced by the electron stream.

Example 4

The relativistic heavy ion collider (RHIC) electron beam ion source (EBIS) at Brookhaven National Laboratory has an ion trap capacity of 1.1×10$^{12}$ charges. This is sufficient to produce the required total extracted ion charge of 5.5×10$^{11}$. To provide primary low charged ion beams to RHIC-EBIS, the LIS must induce 1.7×10$^{10}$ of Au$^{1+}$.

Empirical charge distributions of five ions (Al, Si, Fe, Ta, Au) are assumed to obtain a ratio of total charge in interesting charge state (ICS) to total extracted ion charge and average charge state (CS) of remaining charge in the drift tube (DT) of RHIC-EBIS. The minimum number of singly charged ions N$_{min}$ for a primary ion provider obtained based on the charge distribution and total extracted ion charge of 5.5×10$^{11}$ in RHIC-EBIS are summarized in Table 1.

TABLE 1

Charge distribution in the DT of RHIC-EBIS and minimum number of 1+ charged ion injected for a primary ion provider.

| | Ion species | | | | |
|---|---|---|---|---|---|
| | Al | Si | Fe | Ta | Au |
| Interesting CS for beam | 13 | 14 | 24 | 30 | 32 |
| % of total charge in ICS in the DT | 50 | 50 | 50 | 20 | 20 |
| Average CS of remaining charge in the DT | 11 | 12 | 22 | 30 | 32 |

TABLE 1-continued

Charge distribution in the DT of RHIC-EBIS and minimum number of 1+ charged ion injected for a primary ion provider.

| | Ion species | | | | |
|---|---|---|---|---|---|
| | Al | Si | Fe | Ta | Au |
| Min. # of 1+ ion injected $N_{min}$ ($10^{10}$) | 4.6 | 4.3 | 2.4 | 1.8 | 1.7 |
| LEBT limited peak current $I_p$ [μA] | 68 | 66 | 26 | 30 | 25 |

Table 1 also shows the limited peak current in low energy beam transport (LEBT) for RHIC-EBIS, assuming that the limited peak current is 25 μA for an Au target. Within this limitation, KOBRA simulations (KOBRA3-INP, INP, Junkernstrasse 99, 65205 Wiesbaden, Germany) show good beam transmission in LEBT for RHIC-EBIS. The limited current Ip is proportional to m−½, where m is an atomic mass.

Figure 11A:
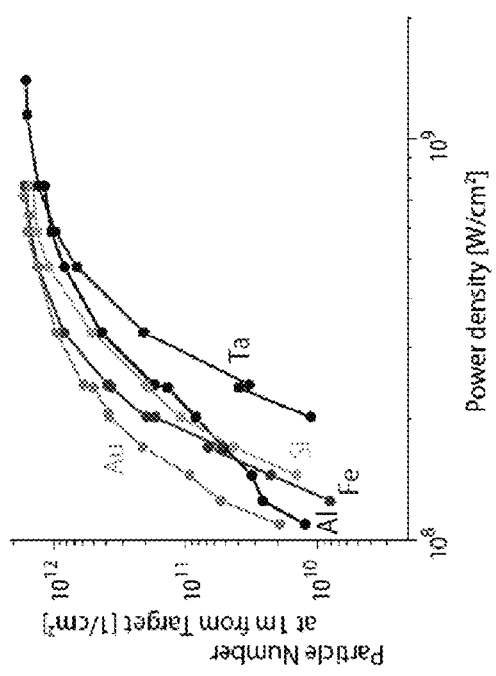
FIG. 11A illustrates a particle number (mostly singly charged ions) at 1 m from the target as a function of laser power density.
Figure 11B:
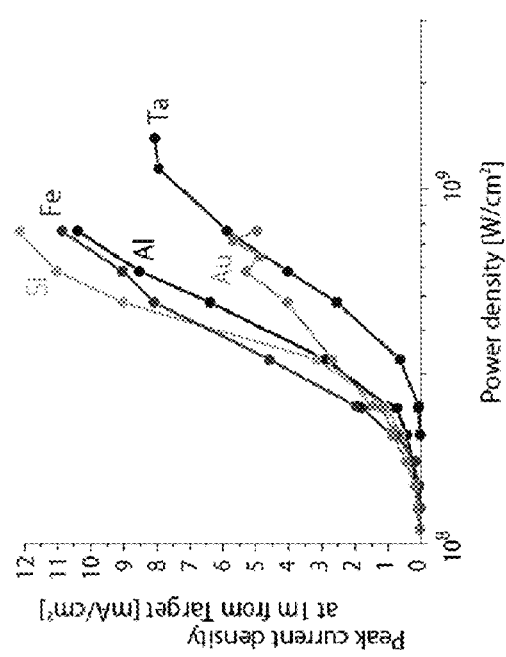
FIG. 11B illustrates a peak current density at 1 m from the target as a function of power density.

A second harmonic, defocused Nd:YAG laser with 0.5 J/6 ns and 532 nm wavelength was used to produce C 1+ ion dominant plasma (Kanesue et al. (*Rev. Sci. Instrum.* 79, 2008, incorporated herein by reference in its entirety). The laser power density with a laser energy (0.5 J) was reduced to keep a sufficient total charge number with longer pulse length to meet the RHIC-EBIS requirement. As in Examples 2 and 3, the ablation plasma was expanded adiabatically from a solid target irradiated by a laser and the total plasma current was measured by a Faraday cup (FC), which was located at the center of the beam line. A cylindrical electrostatic ion analyzer and a secondary electron multiplier (SEM) for measuring the charge state distribution were placed downstream of the faraday cup. The ion signal produced by SEM was calibrated by comparing the sum of each charge state signal multiplied by its charge state to faraday cup total current. FIGS. 11A and 11B represent, respectively, particle number and peak current to laser power density on the solid target. The particle number and peak current were converted per square centimeter at 1 m from the target. The proportion of singly charged ions realized was over 95% based on the condition of laser power density shown in FIGS. 11A and 11B. The particle number is enough for RHIC-EBIS requirement; however, the peak current is too high for LEBT current limit by space charge effect as shown in Table 1 and FIGS. 11A & 11B.

Example 5

A solenoid generated magnetic field was applied at the drift space of the LIS to obtain appropriate low peak current with adequate particle number. In an exemplary configuration shown in FIG. 12A, the drift distance L from solid target to extraction was set to about 5 m. The laser was positioned at the incident angle of 30° and had 0.5 J/6 ns energy output at 532 nm wavelength. The laser power density was set to 2.0× $10^8$ W/cm². A laser spot size of 7 mm was fixed on the target. Table 2 summarizes beam properties at drift distance of 5 m for 5 different ions. The overall efficiency β is defined as the required ratio between the net ion number before and after RHIC-EBIS.

TABLE 2

Beam properties at drift distance of 5 m for RHIC-EBIS.

| | Ion species | | | | |
|---|---|---|---|---|---|
| | Al | Si | Fe | Ta | Au |
| Pulse length t (μs) | 190 | 180 | 220 | 280 | 430 |
| Enhancement factor α | 11 | 15 | 6.6 | 116 | 3.6 |
| Average CS of remaining charge in the DT | 11 | 12 | 22 | 30 | 32 |
| # of 1+ charges injected $N_0$ ($10^{10}$) | 6.1 | 6.5 | 5.2 | 5.2 | 5.3 |
| Overall efficiency β % | 75 | 66 | 46 | 35 | 32 |

Figure 12A:
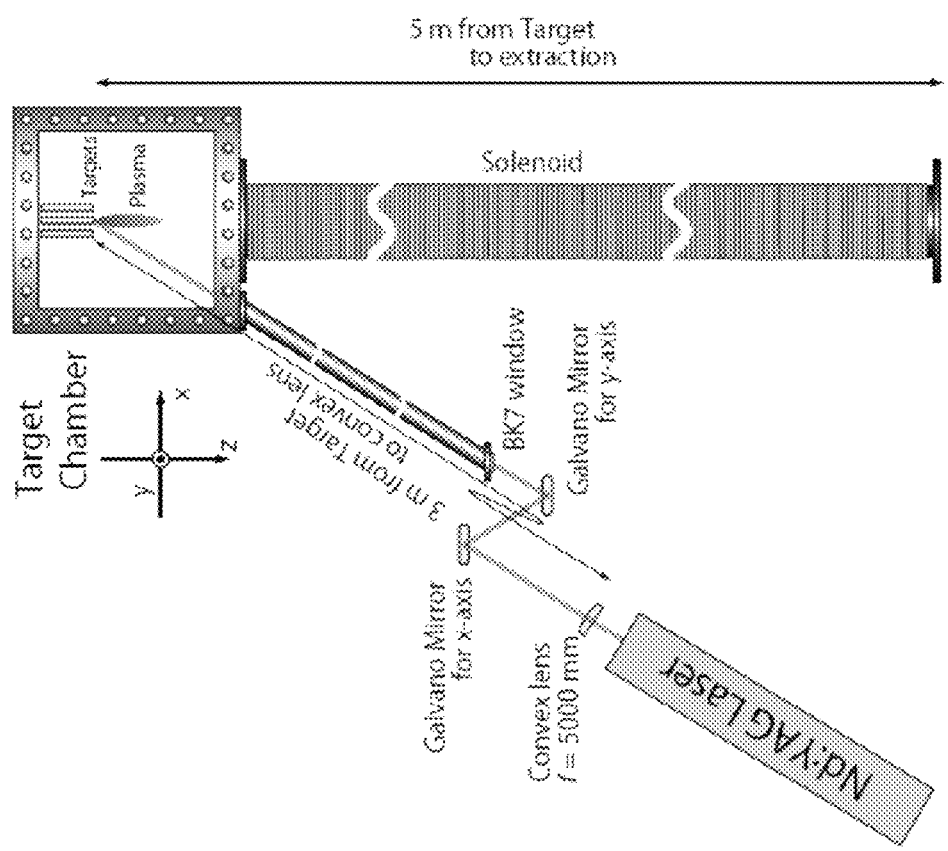
FIG. 12A illustrates an exemplary non-DPIS laser ion source with a solenoid.
Figure 12B:
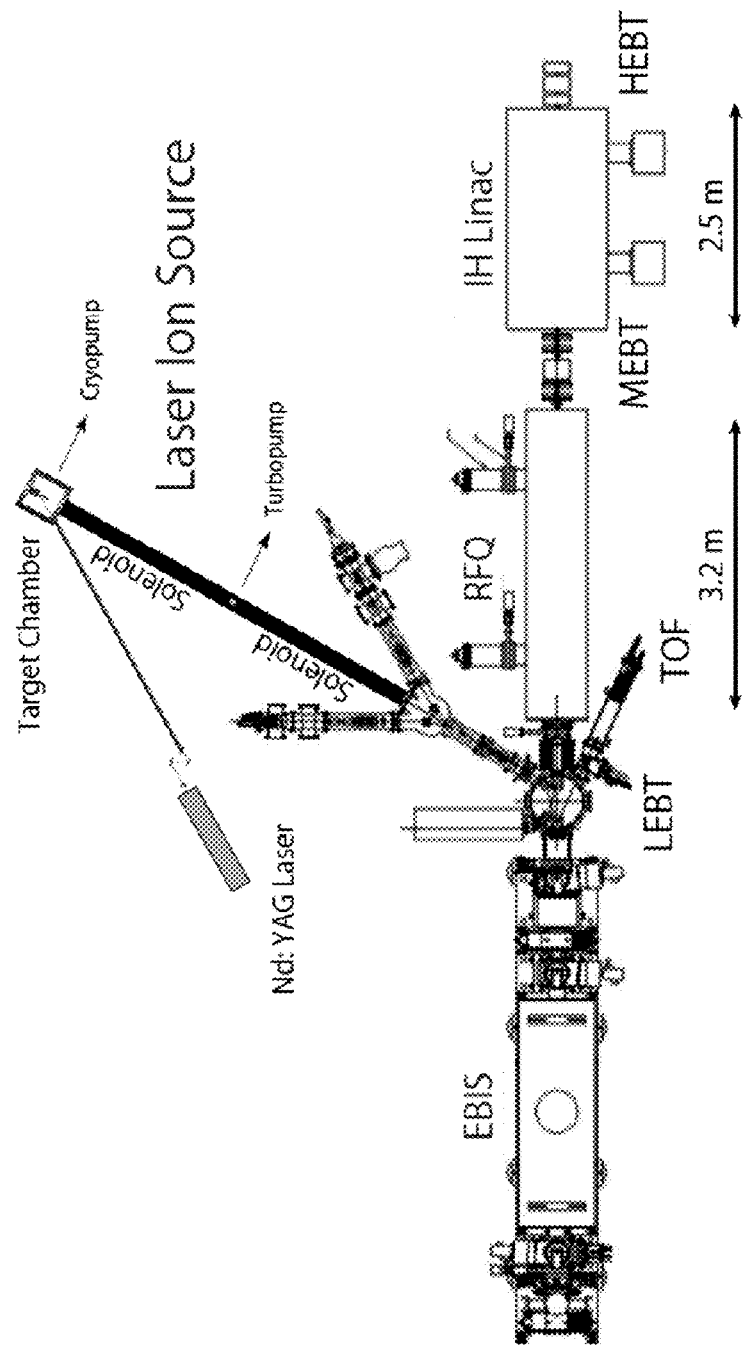
FIG. 12B illustrates RHIC-EBIS preinjector with LIS of FIG. 12A.

The overall optics arrangement is shown in FIG. 12A. Specifically, a convex lens with long focal length (f=5000 mm) was selected and positioned out of and far from the vacuum target chamber to prevent damage of the optics from laser ablation. The distance from the target to the focus lens was 3 m. Two Galvano mirrors for the x and y axis were used because the targets were arranged concentrically on z-plane to keep a small displacement from targets to center of beam line. With a laser power density of 2.4×$10^8$ W/cm² and laser spot size of 7.6 mm for Fe, the crater depth on the Fe target was about 0.02 mm per 30 min at 5 Hz repetition rate. Target rods of 10 cm size were sufficient for the real continuous operation of six months. Heating of the target by laser was not a serious problem in real continuous repetition. FIG. 12B illustrates an exemplary RIHC-EBIS preinjector with the present LIS.

Example 6

A beam property and target consumption for the laser power density with 5 Hz repetition rate in 1 hour operation was examined in this example. An aluminum target (45 mm×45 mm with 1 mm thickness) in the vacuum chamber was irradiated by a Nd:YAG laser at 1064 nm (λ) with 7 ns pulse length. The partially defocused laser generated 6 mm spot size on an Al target using a convex mirror (f=2500 mm) at an incident angle between laser path and beam line of about 30°. The laser path from window to vacuum chamber was set to about 2 m to keep the optics (window) in LIS from being damaged by laser ablation.

Three (3) different laser power densities: 2.2×$10^8$, 2.8×$10^8$, and 3.1×$10^8$ W/cm² were examined. The Faraday Cup (FC) with 5 mm aperture was positioned at 1.95 m from the Al solid target to measure the beam current. The suppressor voltage of the faraday cup was set between about 1.5 kV and about 5.3 kV to avoid a discharge inside the faraday cup. No change of the FC signal was observed in the voltage region.

Figure 13A:
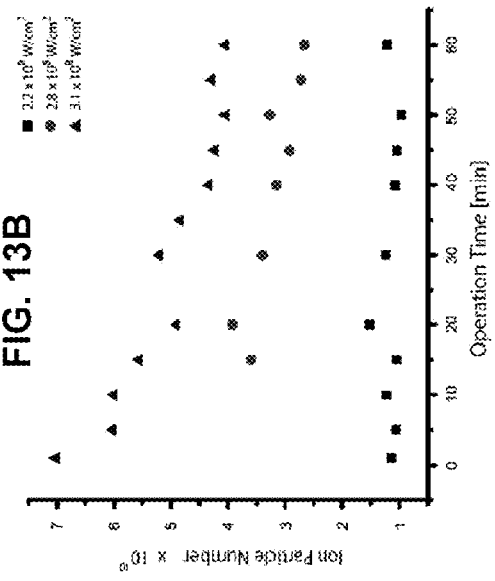
FIG. 13A illustrates a relationship between a beam current and the operation time for 3 types of laser power density with 5 Hz repetition ratio.

A relationship between beam current at FC and the operation time for laser power density is shown in FIG. 13A. In high power density of 3.1×$10^8$ W/cm², the beam current was significantly reduced by 50% with operation time. The decay of beam current was also observed in 2.8×$10^8$ W/cm². Conversely, the beam current kept constant over 1 hour operation when using a low power density of 2.2×$10^8$ W/cm².

Figure 13B:
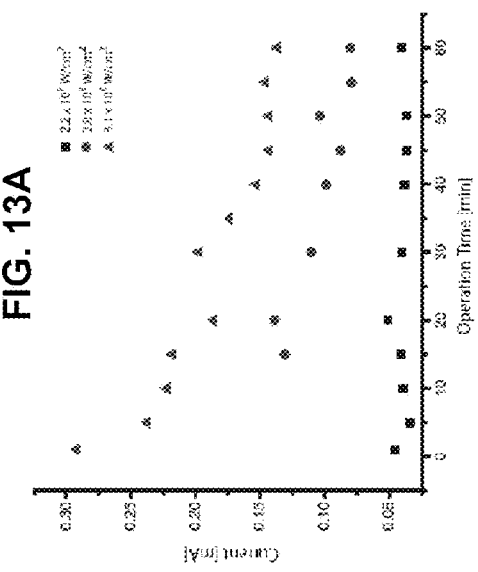
FIG. 13B illustrates vs. operation type for a relationship between a number of particles and the operation time for 3 types of laser power density with 5 Hz repetition ratio.

The beam current ion particle number per 1 (a single) laser shot provided in FIG. 13B shows similar behavior as seen in FIG. 13A with respect to the operation time. These experimental results show that the low laser power density condition is suitable for supplying a constant beam property.

Figure 13C:
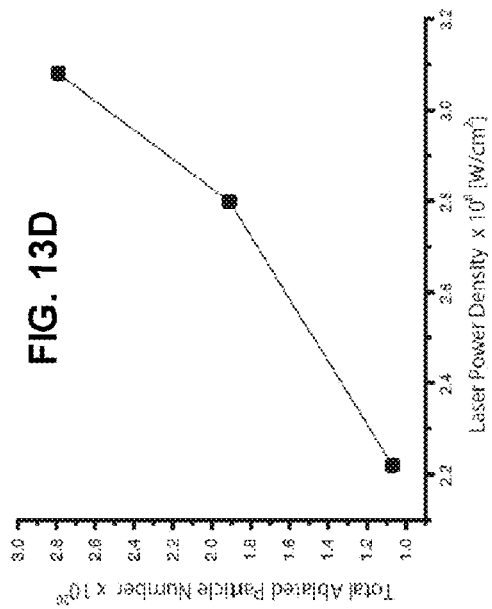
FIG. 13C illustrates a relationship between FWHM and the operation time for 3 types of laser power density with 5 Hz repetition ratio.

FIG. 13C illustrates the Full Width at Half Maximum (FWHM) of the beam as a function of the operation time. Although the FWHMs of initial operation were shorter in length at 2.8×$10^8$ and 3.1×$10^8$ W/cm², they became wider with the passage of time. In the low power density of 2.2×$10^8$ W/cm², the FHWM appears constant (see FIG. 13C). These experimental results show that the FWHM is steady even after, and under long operation time in low power density conditions.

Figure 13D:
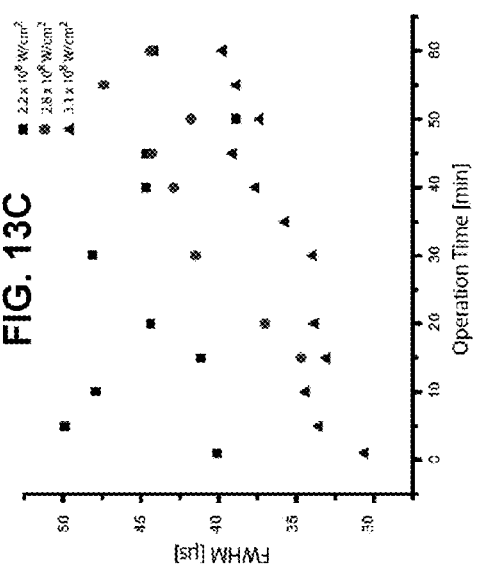
FIG. 13D illustrates a relationship between an ablated particle number in 1 hour of operation and the laser power density.

The weight of the Al target for each laser power density was measured before and after the experiment after 1 (one) hour of operation. The total plasma particle number, which corresponds to the consumption weight, for the laser power density is shown in FIG. 13D. The results show that the consumption amount increased as the laser power density increased.

Figure 14:
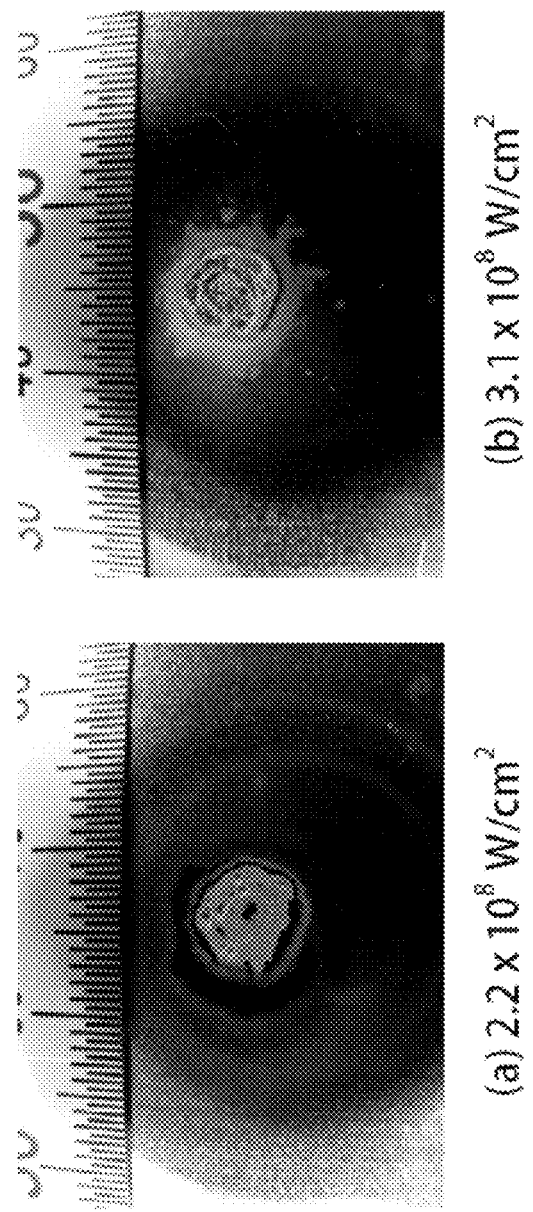
FIG. 14 illustrates an Aluminum surface after 1 hour of operation with 5 Hz repetition ratio; (a) $2.2 \times 10^8$ W/cm$^2$ and (b) $3.1 \times 10^8$ W/cm$^2$.

The Al target surfaces in $2.2\times10^8$ and $3.1\times10^8$ W/cm² are shown in FIG. 14. The surface irradiated with the high laser power density beam is rougher than the surface irradiated with the low laser power density beam, when the beam is kept constant. Since the surface condition depends on the irradiation source, the ablation plasma condition will change, which in turn will cause the change in the property of the produced beam such as the current, the number of ion and the FWHM.

Example 7

Figure 15:
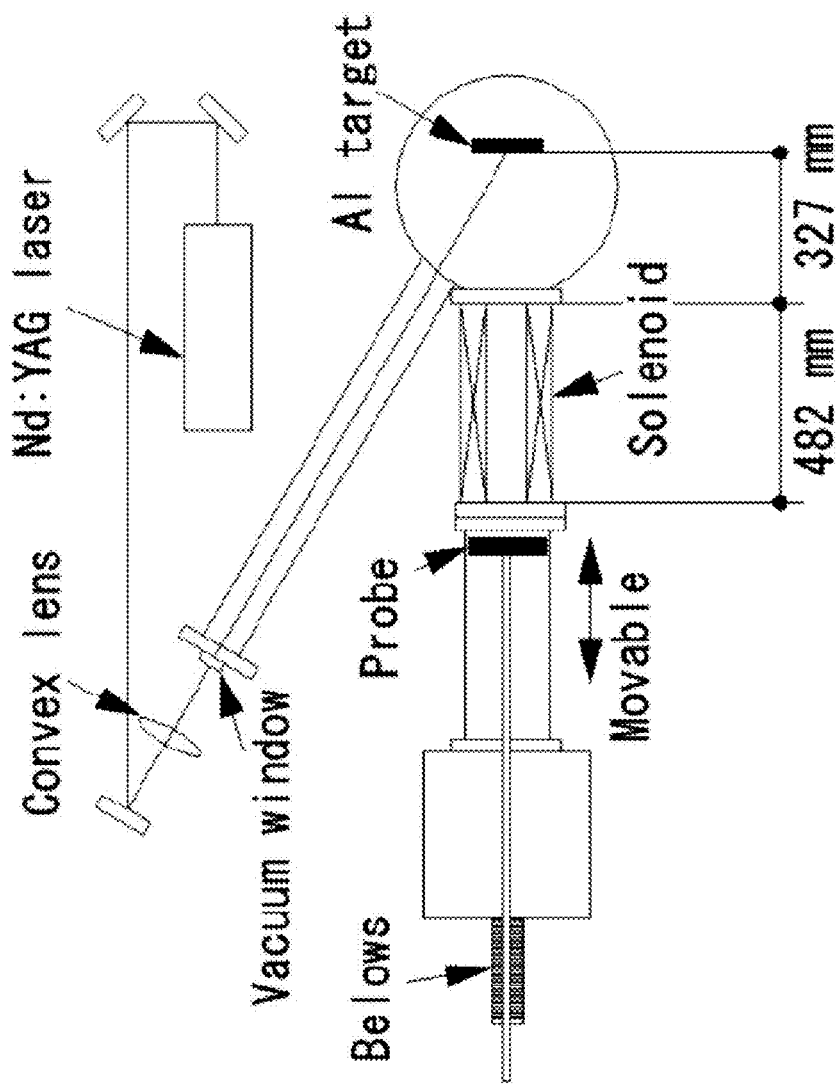
FIG. 15 illustrates a schematic view of an exemplary experimental setup of the LIS system.

FIG. 15 is a schematic of yet another experimental configuration. In this experiment, an Aluminum (Al) target and a second harmonics Nd:YAG laser with wave length of 532 nm were used. The laser energy and the pulse width were 0.56 J and 6 ns, respectively. The laser light was partially focused by a convex mirror (f=2500 mm) and the laser spot size was 6.0 mm. The estimated laser power density was $3.5\times10^8$ W/cm², where more than 95% of ions were singly charged ions based on the experiment provided in Example 6.

Figure 16:
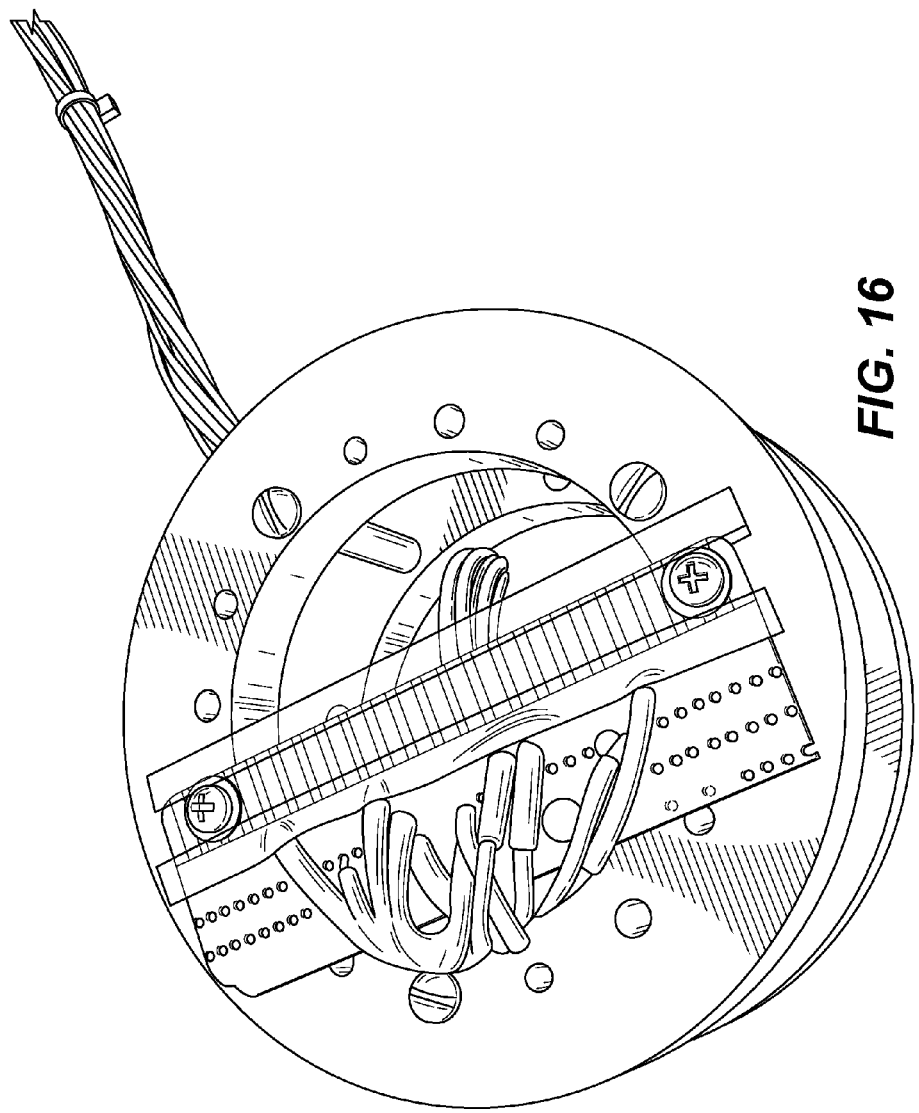
FIG. 16 illustrates a probe used in the transverse distribution measurements.

Singly charged ions were used to understand the ion distribution. A solenoid magnet which had a length of 482 mm and an inner diameter of 76 mm was placed at a distance of 326.5 mm from the target. A special probe shown in FIG. 16 was designed to measure a transverse distribution of ions. This detector had nine detection points of small metal plates along the perpendicular to the beam line. These detection points were masked by an insulation sheet which had nine apertures of 0.75 mm in diameter corresponding to the position of the detection points. Since this probe was several millimeters smaller than the beam line, the center of the probe was not the same as the center of the beam pipe. Table 3 shows the measured distance between the detection points and the beam line.

TABLE 3

| Transverse position of probe detection point. | | | | | | | | | |
|---|---|---|---|---|---|---|---|---|---|
| | Detection points | | | | | | | | |
| | No. 1 | No. 2 | No. 3 | No. 4 | No. 5 | No. 6 | No. 7 | No. 8 | No. 9 |
| Radius (mm) | −29.2 | −20.9 | −13.2 | −5.6 | −0.9 | 3.0 | 11.2 | 18.9 | 27.0 |

The detection plate was biased to −100 V to prevent electrons from hitting the plates during the experiment. This probe was able to move 120 mm along the beam axis. The minimal distance between the end of the solenoid magnet and the probe was 22.5 mm.

Figure 17B:
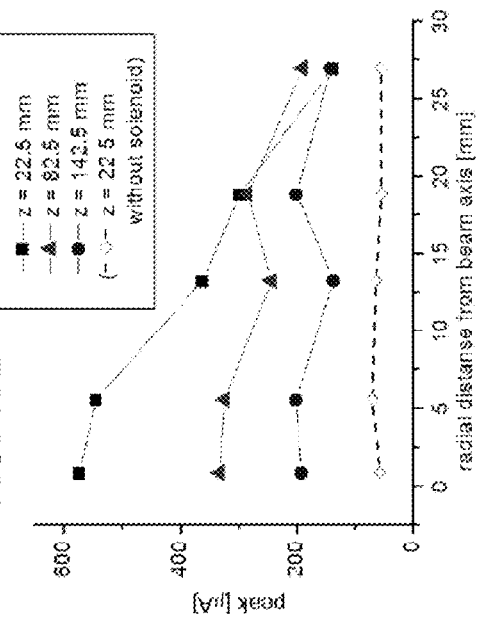
FIG. 17B illustrates transverse ion distribution with solenoid field of 0 and 154 gauss.
Figure 17C:
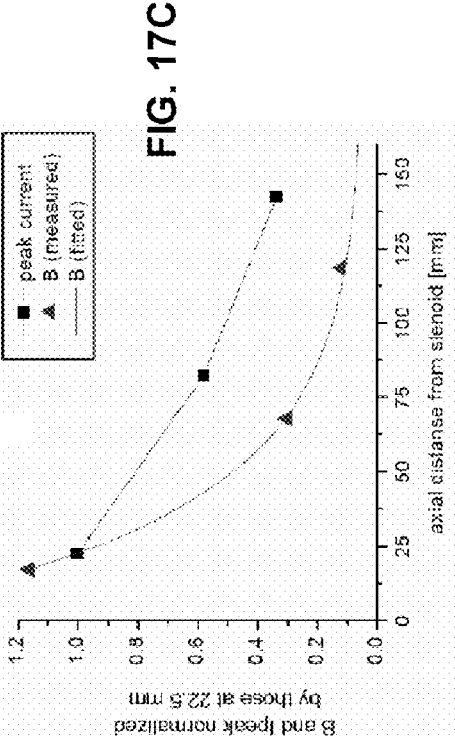
FIG. 17C illustrates a solenoid field and peak current at the center of the probe shown in FIG. 16.
Figure 17A:
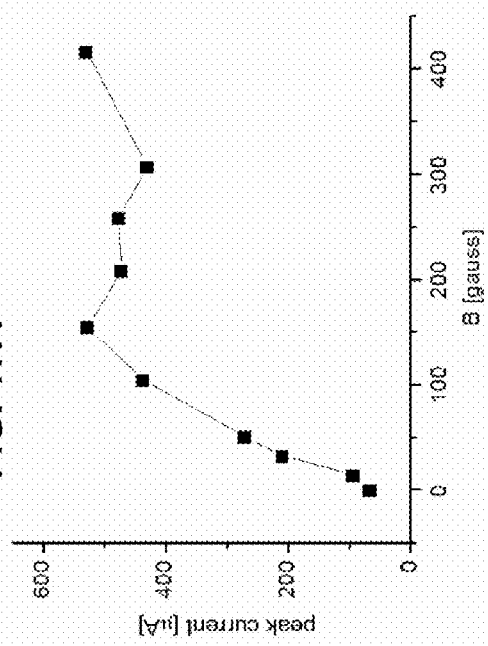
FIG. 17A illustrates a solenoid field and peak current at the center of the probe shown in FIG. 16.

As the solenoid field was increased from 0 to 154 gauss, the peak current measured at the center of the probe, at 22.5 mm downstream of the solenoid, increased almost linearly, until the current enhancement was saturated at a factor of eight when the solenoid field of more than 154 gauss was applied (see FIG. 17A). Subsequently, an ion distribution in a transverse direction under the fixed solenoid field of 154 gauss was examined. One of the detection points at the same transverse position was used during these experiments, because the transverse distribution using all of the detection points on the probe showed good axial symmetrical distribution.

FIG. 17B shows the transverse distributions at 22.5 mm, 82.5 mm and 142.5 mm from the solenoid magnet, respectively. The transverse distribution at 22.5 mm without the solenoid field is also plotted in FIG. 17B as a dashed line. At 22.5 mm from the solenoid, the detected current, without the solenoid field, was about 60 µA over the detection points. With a solenoid field of 154 gauss, the highest current was measured at the center of the probe and the current decreased at off-center points because of the confinement by the solenoid field. Full width at half maximum of beam was 36 mm. At 82.5 mm and 142.5 mm far from the solenoid magnet, the measured distributions were similar and these were wide and flat transverse distributions. Overall, the effect of the solenoid field was observed in all of the measured ranges.

FIG. 17C shows the peak current at a radius of 0.9 mm from the beam axis and the measured magnetic field strength at 22.5 mm, 82.5 mm and 142.5 mm from the solenoid. Both, the peak current and the magnetic field strength, are normalized by the value at 22.5 mm from the solenoid magnet, respectively. Although, both were decreased at increased distances from the solenoid, the reduction of the peak current was smaller than that of the magnetic field strength.

The enhancement factor of eight in this experiment was smaller than forty measured in Example 6. This can be explained by the fact that the distance between a target and a solenoid magnet in this experiment (326.5 mm) was longer than that in Example 6 (295 mm). The increased distance (326.5 mm) of the solenoid allowed the plasma to expand longer and as a result, the amount of plasma that was captured by the solenoid field decreased. This result indicates that the effect of the solenoid field is strongly related to the position of the solenoid magnet to the target.

Based on the time of flight of the ions, the kinetic energy of electrons was estimated up to about 0.03 eV. Even if electron motion is perpendicular to the magnetic field line, the Larmor radius at 154 gauss is about 40 µm, which means that the electrons travel along the field line. This experiment confirmed that the strong effect of the solenoid field exists within 27 mm in the transverse direction and 142.5 mm in the longitudinal direction from the beam axis.

Example 8

Figure 18:
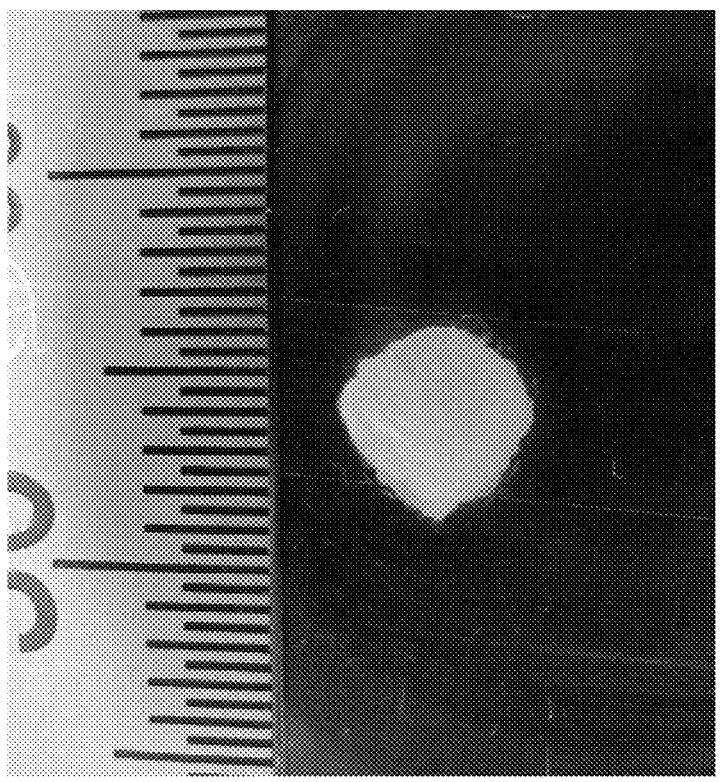
FIG. 18 illustrates a silver place used as a target in the DPIS system shown in FIG. 2A.
Figure 19A:
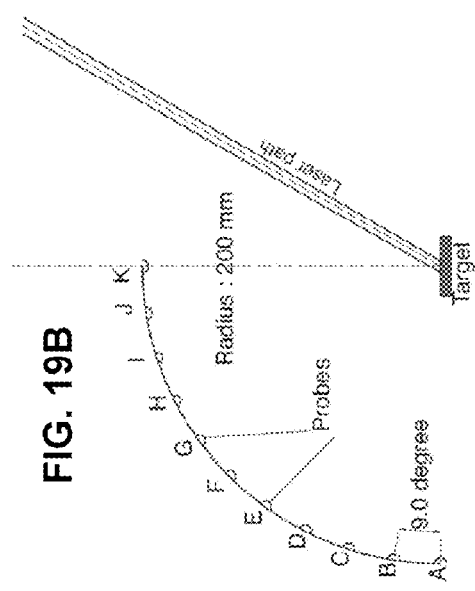
FIG. 19A illustrates a laser pulse profile used in the DPIS system shown in FIG. 2A.

Silver (Ag) was used as a laser target material for yet another experimental configuration, since it is relatively easy to produce a stable laser induced plasma on a silver target. To simplify the experiment, single charge state ions were created by choosing a low laser power density on the target. FIG. 18 shows a footprint of multiple laser shots on a pure silver plate. The laser spot diameter was measured as 4.5 mm. The Nd—YAG laser with 416 mJ of laser power was used with a second harmonics crystal (λ: 532 nm). The laser pulse duration was measured as 6.1 ns, as indicated in FIG. 19A. The estimated laser power density was $4.3\times10^8$ W/cm². At this laser power density, most of the ions are expected to be singly charged according to Kanesue et al. (Proceedings of EPAC 08, 2008, p. 421; incorporated here by reference in its entirety)

Figure 19B:
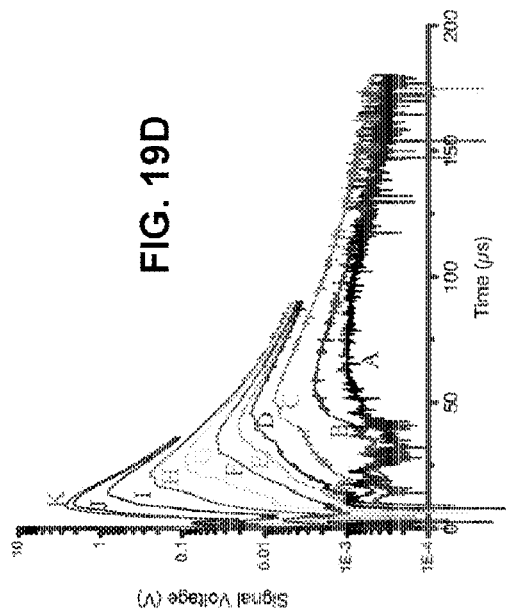
FIG. 19B illustrates a layout of eleven langmuir probes used to detect the ion currents in the expanding plasmas.

Eleven Langmuir probes were used to detect the ion currents in the expanding plasmas. Each sensing area had a round shape and a diameter of 3.33 mm. The probes were biased at 50 V and the measured signals were within ion saturation region. The array was installed horizontally and each detector was positioned every 9 degrees, as illustrated in FIG. 19B. The incident angle of the laser path was set at 30 degrees with respect to a line or plane perpendicular to the target surface.

Figure 19C:
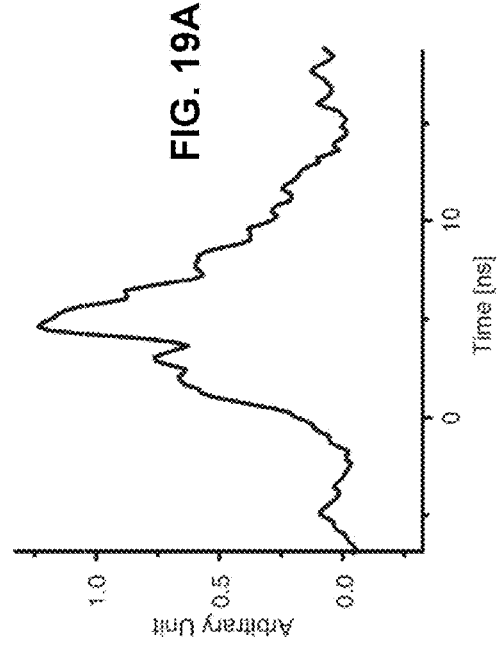
FIGS. 19C and 19D illustrate a current distribution in linear (A) and log (B) scale.
Figure 19D:
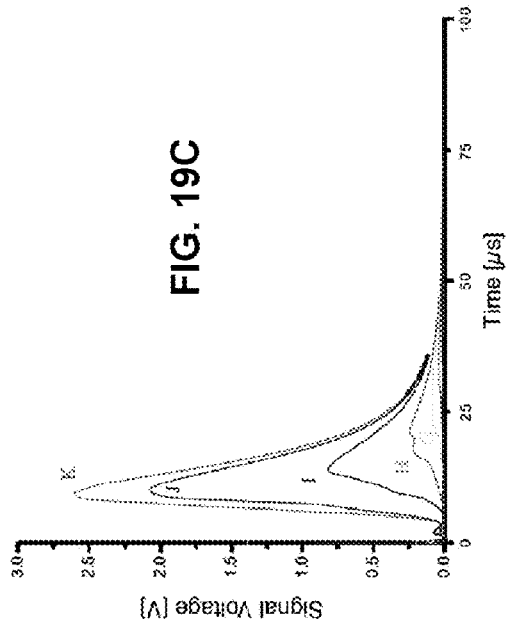
Figure 20A:
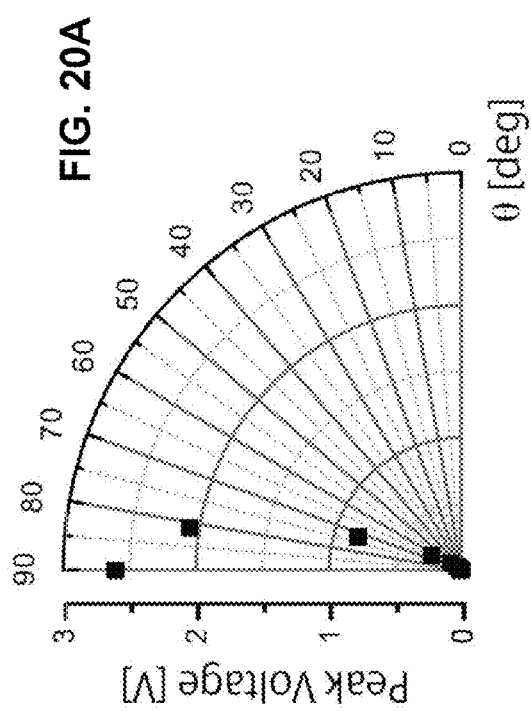
FIG. 20A illustrates the directivity of plasma expansion.

The induced signal voltages at a 50Ω terminating register are shown in FIGS. 19C and 19D. Both graphs are identical with different vertical scales, linear and log. A 1 V reading corresponds to 230 mA/cm². At the position "K", the normal position, the maximum current was observed. At an angle of more than 30 degrees, the current was significantly reduced. In the horizontal scales, the laser beams were used as a trigger signal at t=0. The plasma expansion velocity was slower at deeper angle positions. FIG. 19D illustrates that higher energy ions have sharper directivity. FIG. 20A shows the directivity of the plasma expansion. Each point represents the peak value of the recorded current. Based on this data, ±10-15 degrees of the acceptance seems reasonable to maximize the ion capturing efficiency.

Figure 20B:
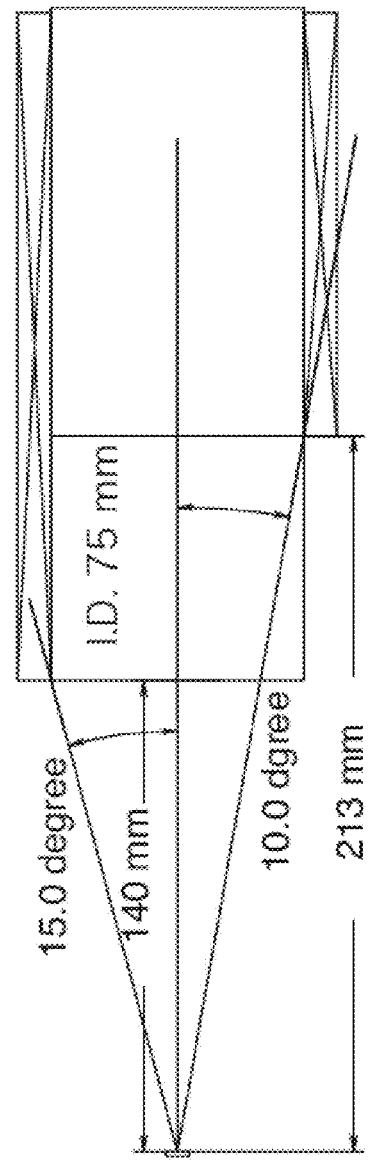
FIG. 20B illustrates an exemplary scheme of determining the positioning of the solenoid based on the directivity of the plasma expansion.

The current enhancement by a solenoid generated magnetic field is severely affected by the positioning of the solenoid. For instance, as shown in FIG. 20B, in order to have ±10 degrees acceptance a solenoid that has 75 mm of the inner diameter may be installed at 213 mm from the laser target (140 mm for ±15 degrees).

It will be appreciated by persons skilled in the art that the present invention is not limited to what has been particularly shown and described. Rather, the scope of the present invention is defined by the claims which follow. It should further be understood that the above description is only representative of illustrative examples of embodiments. For the reader's convenience, the above description has focused on a representative sample of possible embodiments, a sample that teaches the principles of the present invention. Other embodiments may result from a different combination of portions of different embodiments.

The description has not attempted to exhaustively enumerate all possible variations. The alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent. Furthermore, all references, publications, U.S. patents, and U.S. Patent Application Publications cited throughout this specification are hereby incorporated by reference as if fully set forth in this specification.

The invention claimed is:

1. A laser ion source, comprising
   a repetitively-pulsed laser producing pulses with duration from about 5 to 100 ns;
   an electrically isolated enclosure;
   a plasma target confined within the enclosure;
   a plasma drift section connected to the enclosure;
   an ion linear accelerator connected to the plasma drift section, and
   a rapid beam current controller positioned in the plasma drift section between the enclosure and the ion linear accelerator,
   wherein the rapid beam current controller generates a magnetic field in the plasma drift section to confine a plasma flux caused by a laser ablation, the plasma flux comprising ions guided by an electrical potential induced by an electron stream.

2. The laser ion source according to claim 1, further configured into a direct plasma injection scheme (DPIS).

3. The laser ion source according to claim 1, wherein the rapid beam current controller is a solenoid.

4. The laser ion source according to claim 3, wherein the solenoid has a diameter between 10 mm and 500 mm and a length between 10 mm and 10 m as measured in the direction of a longitudinal axis of the solenoid.

5. The laser ion source according to claim 4, wherein the diameter of the solenoid is about 100 mm.

6. The laser ion source according to claim 3, wherein the solenoid comprises a helically wound wire with a diameter of 0.1 mm to about 10 mm.

7. The laser ion source according to claim 1, wherein the ratio of the plasma drift section length to the rapid beam current controller length is between about 1:1 and 10:1.

8. The laser ion source according to claim 7, wherein the ratio of the plasma drift section length to the rapid beam current controller length is about 3:1.

9. The laser ion source according to claim 1, wherein the rapid beam current controller generates a magnetic field greater than 50 gauss.

10. The laser ion source according to claim 1, wherein the plasma drift section has an inner diameter and an outer diameter.

11. The laser ion source according to claim 10, wherein the plasma drift length is about 5 m.

12. The laser ion source according to claim 1, wherein the rapid beam current controller encircles the outer diameter of the plasma drift section between the electrically isolated enclosure and the ion linear accelerator.

13. The laser ion source according to claim 12, wherein the inner diameter of the rapid beam current controller is substantially the same as the outer diameter of the plasma drift section.

14. The laser ion source according to claim 1, wherein the distance between the plasma target and the ion linear accelerator is a plasma drift length.

15. The laser ion source according to claim 1, wherein the plasma drift length is about 200 mm to about 10 m.

16. The laser ion source according to claim 1, wherein the longitudinal size of the rapid beam current controller is substantially the same as the plasma drift section connecting the electrically isolated enclosure and the ion linear accelerator.

17. The laser ion source according to claim 1, wherein the longitudinal size of the rapid beam current controller is shorter than the plasma drift section connecting the electrically isolated enclosure and the ion linear accelerator.

18. The laser ion source according to claim 1, wherein the target comprises graphite or Ti—H.

19. The laser ion source according to claim 1, wherein the target comprises Al, Si, Fe, Ta, Ag, Au, Ge, Pb, Cu, Ti, Pt, U, frozen Ne, or frozen Ar.

20. The laser ion source according to claim 1 further comprises a repetitively-pulsed laser that irradiates the target to produce a plasma ablation.

21. The laser ion source according to claim 20, wherein the repetitively-pulsed laser has a power density between $10^8$ and $10^{13}$ W/cm2.

22. The laser ion source according to claim 20, wherein the repetitively-pulsed laser is a $CO_2$, Nd—YAG or Ti:Sapphire laser.

23. The laser ion source according to claim 20, further comprises one or more lenses and one or more mirrors positioned between the laser and the target to guide the laser light from the laser to the target.

24. The laser ion source according to claim 23, wherein the minors and lenses are positioned outside the enclosure.

25. The laser ion source according to claim 23, wherein some of the mirrors and the lenses are positioned inside the enclosure.

26. The laser ion source according to claim 1, wherein the electrically isolated enclosure comprises a stainless steel.

27. The laser ion source according to claim 1, wherein the pressure within the electrically isolated enclosure is less than 10-5 Torr.

28. The laser ion source according to claim 1, wherein the pressure within the electrically isolated enclosure is between 10-5 and 10-7 Torr.

29. The laser ion source according to claim 1, wherein the rapid beam current controller is positioned between the electrically isolated enclosure and the ion linear accelerator with an acceptance angle from about ±10 to about ±15 degrees.

30. The laser ion source of claim 1, wherein the ion linear accelerator is a radio frequency quadrupole (RFQ) linac.

31. The laser ion source according to claim 1, wherein the enclosure and the ion linear accelerator each independently comprises an opening aligned with a cavity of the plasma drift section.

32. The laser ion source according to claim 31, wherein the opening on the enclosure and the opening on the ion linear accelerator are aligned to allow a plasma to pass from the target to a RFQ cavity.

33. A method of controlling diverging angles of a laser plasma in a laser ion source, comprising
generating a laser plasma in the form of laser pulses with duration from about 5 to 100 ns on a surface of a target by plasma ablation confined within an electrically isolated enclosure;
allowing the generated laser plasma to pass through a plasma drift section into a cavity of an ion linear accelerator, wherein the plasma drift section comprises a rapid beam current controller to confine the laser plasma, the laser plasma comprising ions guided by an electrical potential induced by an electron stream; and
adjusting the diverging angles of the laser plasma by changing the magnetic field strength of the rapid beam current controller.

34. A method of regulating a beam current and a pulse shape in the laser ion source, comprising
regulating the beam current and the pulse shape in the laser ion source by adjusting the diverging angles of the laser plasma according to claim 33.

35. A method of controlling a number of particles in a synchrotron comprising
adjusting the number of particles reaching the linear accelerator by adjusting the diverging angles of the laser plasma according to claim 33;
extracting a plurality of ions from the generated plasma by an electric field in the ion linear accelerator;
capturing generated ions on a pulse by pulse basis by a radio frequency quadrupole focusing force;
accelerating the generated ions in the ion linear accelerator; and
injecting the accelerated ions into a synchrotron.

36. A method of controlling a number of particles in a synchrotron according to claim 35, wherein the synchrotron is a rapid cycling synchrotron.

37. A method of treating cancer using a hadron therapy comprising
generating a laser plasma in the form of laser pulses with duration from about 5 to 100 ns on the surface of a target by plasma ablation confined within an electrically isolated enclosure;
allowing the generated laser plasma to pass through a plasma drift section into a cavity of an ion linear accelerator, wherein the plasma drift section comprises a rapid beam current controller to confine the laser plasma, the laser plasma comprising ions guided by an electrical potential induced by an electron stream;
adjusting the number of ion particles reaching the linear accelerator by changing a magnetic field strength of the rapid beam current controller;
extracting a plurality of ions from the generated plasma by an electric field in the ion linear accelerator;
capturing generated ions on a pulse by pulse basis by a radio frequency quadrupole focusing force;
accelerating the generated ions in the ion linear accelerator;
injecting the accelerated ions into a synchrotron;
accelerating the injected ions by the synchrotron up to desired ion beam energy;
diverting and passing the ions through a medical gantry towards a patient in need of treatment; and
irradiating a cancerous tissue in the patient with the generated ions.

38. A method of controlling a number of particles in a synchrotron according to claim 37, wherein the synchrotron is a rapid cycling synchrotron.

* * * * *